US012186067B2

(12) United States Patent
Lyu et al.

(10) Patent No.: US 12,186,067 B2
(45) Date of Patent: Jan. 7, 2025

(54) SYSTEMS AND METHODS FOR MAGNETIC RESONANCE IMAGING

(71) Applicant: SHANGHAI UNITED IMAGING HEALTHCARE CO., LTD., Shanghai (CN)

(72) Inventors: Jingyuan Lyu, Houston, TX (US); Qi Liu, Houston, TX (US); Yongquan Ye, Houston, TX (US); Jian Xu, Houston, TX (US); Zhongqi Zhang, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 317 days.

(21) Appl. No.: 17/645,753

(22) Filed: Dec. 23, 2021

(65) Prior Publication Data

US 2022/0409084 A1 Dec. 29, 2022

Related U.S. Application Data

(63) Continuation-in-part of application No. 17/304,652, filed on Jun. 24, 2021.

(51) Int. Cl.
A61B 5/055 (2006.01)
G01R 33/48 (2006.01)
G01R 33/561 (2006.01)

(52) U.S. Cl.
CPC ............ *A61B 5/055* (2013.01); *G01R 33/482* (2013.01); *G01R 33/5611* (2013.01); *G01R 33/5616* (2013.01); *G01R 33/5617* (2013.01)

(58) Field of Classification Search
CPC .. A61B 5/055; G01R 33/482; G01R 33/5611; G01R 33/5616; G01R 33/5617
See application file for complete search history.

(56) References Cited

U.S. PATENT DOCUMENTS 8,981,776 B2   3/2015   Setsompop et al.
10,436,871 B2  10/2019  Li et al.
(Continued)

FOREIGN PATENT DOCUMENTS

CN   103519816 B   8/2015
CN   110133555 A   8/2019
CN   115251884 A   11/2022

OTHER PUBLICATIONS

Jesse Hamilton et al., Recent Advances in Parallel Imaging for MRI, Progress in Nuclear Magnetic Resonance Spectroscopy, 101: 71-95, 2017.
(Continued)

*Primary Examiner* — Sean A Frith
(74) *Attorney, Agent, or Firm* — METIS IP LLC

(57) ABSTRACT

A method may include obtaining a plurality of imaging signals collected by applying a wave encoding gradient to a region of interest (ROI) of a subject. The method may also include obtaining a plurality of auxiliary signals associated with the ROI. The method may also include obtaining a point spread function corresponding to the wave encoding gradient. The method may also include determining, based on the plurality of auxiliary signals, temporal information relating to at least one temporal dimension of the ROI. The method may also include determining, based on the plurality of auxiliary signals, the plurality of imaging signals, and the point spread function, spatial information relating to at least one spatial dimension of the ROI. The method may also include generating at least one target image of the ROI based on the temporal information and the spatial information.

20 Claims, 10 Drawing Sheets

(56) References Cited

U.S. PATENT DOCUMENTS

| | | | |
|---|---|---|---|
| 11,035,920 B2 | 6/2021 | Wald et al. | |
| 2013/0099784 A1* | 4/2013 | Setsompop | G01R 33/543 |
| | | | 324/309 |
| 2015/0077112 A1* | 3/2015 | Otazo | A61B 5/7207 |
| | | | 324/318 |
| 2018/0143277 A1* | 5/2018 | Chen | G01R 33/5611 |
| 2018/0189930 A1 | 7/2018 | Dannels | |
| 2019/0250237 A1* | 8/2019 | Boernert | G01R 33/3852 |
| 2020/0090382 A1 | 3/2020 | Huang et al. | |
| 2020/0357149 A1 | 11/2020 | Nagashima et al. | |
| 2020/0405176 A1* | 12/2020 | Nielsen | G01R 33/5612 |
| 2021/0247477 A1 | 8/2021 | Takeshima | |

OTHER PUBLICATIONS

Hisamoto Moriguchi et al., Bunched Phase Encoding (BPE): A New Fast Data Acquisition Method in MRI, Magnetic Resonance in Medicine: An Official Journal of the International Society for Magnetic Resonance in Medicine, 55(3): 633-648, 2006.

Berkin Bilgic et al., Wave-CAIPI for Highly Accelerated 3D Imaging, Magnetic Resonance in Medicine, 73(6): 2152-2162, 2015.

Nan Wang et al., Six-Dimensional Quantitative DCE MR Multitasking of the Entire Abdomen: Method And Application to Pancreatic Ductal Adenocarcinoma, Magnetic Resonance in Medicine, 84(2): 928-942, 2020.

Anthony G. Christodoulou et al., Magnetic Resonance Multitasking for Motion-Resolved Quantitative Cardiovascular Imaging, Nature Biomedical Engineering, 2: 215-226, 2018.

Daniel K. Sodickson et al., Simultaneous Acquisition of Spatial Harmonics (SMASH): Fast Imaging with Radiofrequency Coil Arrays, Magnetic Resonance in Medicine, 38(4): 591-603, 1997.

Klaas P. Pruessmann et al., SENSE: Sensitivity Encoding for Fast MRI, Magnetic Resonance in Medicine: An Official Journal of the International Society for Magnetic Resonance in Medicine, 42(5): 952-962, 1999.

Mark A. Griswold et al., Generalized Autocalibrating Partially Parallel Acquisitions (GRAPPA), Magnetic Resonance in Medicine: An Official Journal of the International Society for Magnetic Resonance in Medicine, 47(6): 1202-1210, 2002.

Felix A. Breuer et al., Controlled Aliasing in Volumetric Parallel Imaging (2D Caipirinha), Magnetic Resonance in 9 Medicine: An Official Journal of the International Society for Magnetic Resonance in Medicine, 55(3): 549-556, 2006.

* cited by examiner

600

```
┌─────────────────────────────────────────────────────┐
│ Obtaining a plurality of imaging signals collected   │ — 610
│ by applying a wave encoding gradient to a region of  │
│ interest (ROI) of a subject, the wave encoding       │
│ gradient including a first oscillating encoding      │
│ gradient in a first direction and a second           │
│ oscillating encoding gradient in a second direction  │
└─────────────────────────────────────────────────────┘
                          ↓
┌─────────────────────────────────────────────────────┐
│ Obtaining a plurality of auxiliary signals           │ — 620
│ associated with the ROI                              │
└─────────────────────────────────────────────────────┘
                          ↓
┌─────────────────────────────────────────────────────┐
│ Obtaining a point spread function corresponding to   │ — 630
│ the wave encoding gradient                           │
└─────────────────────────────────────────────────────┘
                          ↓
┌─────────────────────────────────────────────────────┐
│ Determining, based on the plurality of auxiliary     │ — 640
│ signals, temporal information relating to at least   │
│ one temporal dimension of the ROI                    │
└─────────────────────────────────────────────────────┘
                          ↓
┌─────────────────────────────────────────────────────┐
│ Determining, based on the plurality of auxiliary     │ — 650
│ signals, the plurality of imaging signals, and the   │
│ point spread function, spatial information relating  │
│ to at least one spatial dimension of the ROI         │
└─────────────────────────────────────────────────────┘
                          ↓
┌─────────────────────────────────────────────────────┐
│ Generating at least one target image of the ROI      │ — 660
│ based on the temporal information and the spatial    │
│ information                                          │
└─────────────────────────────────────────────────────┘
```

FIG. 6

SYSTEMS AND METHODS FOR MAGNETIC RESONANCE IMAGING

CROSS-REFERENCE TO RELATED APPLICATIONS

This application is a continuation-in-part of U.S. application Ser. No. 17/304,652, filed on Jun. 24, 2021, the entire contents of which are hereby incorporated by reference.

TECHNICAL FIELD

This disclosure generally relates to magnetic resonance imaging (MRI), and more particularly, relates to systems and methods for image reconstruction in MRI.

BACKGROUND

Magnetic resonance imaging (MRI) systems are widely used in medical diagnose. MRI systems use a powerful magnetic field and radio frequency (RF) techniques to generate images of a subject to be scanned. A wave encoding technique allows to achieve a relatively high acceleration factor of the MRI. A multitasking technique is capable of acquiring MR data of multiple dimensions (e.g., information relating to various physiological motions, relaxations, etc.) in a single MRI scan. Therefore, it is desirable to provide systems and methods that combines the wave encoding technique and the multitasking technique, thereby achieving the advantages of both the wave encoding technique and the multitasking technique.

SUMMARY

According to an aspect of the present disclosure, a system for magnetic resonance imaging (MRI) may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain a plurality of imaging signals collected by applying a wave encoding gradient to a region of interest (ROI) of a subject. The one or more processors may obtain a plurality of auxiliary signals associated with the ROI. The one or more processors may obtain a point spread function corresponding to the wave encoding gradient. The one or more processors may determine, based on the plurality of auxiliary signals, temporal information relating to at least one temporal dimension of the ROI. The one or more processors may determine, based on the plurality of auxiliary signals, the plurality of imaging signals, and the point spread function, spatial information relating to at least one spatial dimension of the ROI. The one or more processors may generate at least one target image of the ROI based on the temporal information and the spatial information.

According to another aspect of the present disclosure, a method for magnetic resonance imaging (MRI) may include one or more of the following operations. One or more processors may obtain a plurality of imaging signals collected by applying a wave encoding gradient to a region of interest (ROI) of a subject. The one or more processors may obtain a plurality of auxiliary signals associated with the ROI. The one or more processors may obtain a point spread function corresponding to the wave encoding gradient. The one or more processors may determine, based on the plurality of auxiliary signals, temporal information relating to at least one temporal dimension of the ROI. The one or more processors may determine, based on the plurality of auxiliary signals, the plurality of imaging signals, and the point spread function, spatial information relating to at least one spatial dimension of the ROI. The one or more processors may generate at least one target image of the ROI based on the temporal information and the spatial information.

According to yet another aspect of the present disclosure, a system for magnetic resonance imaging (MRI) may include an obtaining module configured to obtain a plurality of imaging signals collected by applying a wave encoding gradient to a region of interest (ROI) of a subject, obtain a plurality of auxiliary signals associated with the ROI, and obtain a point spread function corresponding to the wave encoding gradient. The system may also include a determination module configured to determine, based on the plurality of auxiliary signals, temporal information relating to at least one temporal dimension of the ROI, and determine, based on the plurality of auxiliary signals, the plurality of imaging signals, and the point spread function, spatial information relating to at least one spatial dimension of the ROI. The system may also include a reconstruction module configured to generate at least one target image of the ROI based on the temporal information and the spatial information.

According to yet another aspect of the present disclosure, a non-transitory computer readable medium may comprise at least one set of instructions. The at least one set of instructions may be executed by one or more processors of a computer server. The one or more processors may obtain a plurality of imaging signals collected by applying a wave encoding gradient to a region of interest (ROI) of a subject. The one or more processors may obtain a plurality of auxiliary signals associated with the ROI. The one or more processors may obtain a point spread function corresponding to the wave encoding gradient. The one or more processors may determine, based on the plurality of auxiliary signals, temporal information relating to at least one temporal dimension of the ROI. The one or more processors may determine, based on the plurality of auxiliary signals, the plurality of imaging signals, and the point spread function, spatial information relating to at least one spatial dimension of the ROI. The one or more processors may generate at least one target image of the ROI based on the temporal information and the spatial information.

In some embodiments, the wave encoding gradient may lead to a corkscrew trajectory in the k-space.

In some embodiments, the wave encoding gradient may include a first oscillating encoding gradient in a first direction and a second oscillating encoding gradient in a second direction.

In some embodiments, there may be a phase difference between the first oscillating encoding gradient and the second oscillating encoding gradient.

In some embodiments, the plurality of imaging signals may be obtained by filling target magnetic resonance (MR) signals into the k-space with variable densities.

In some embodiments, the plurality of imaging signals may be obtained by filling target magnetic resonance (MR) signals into the k-space with a uniform density.

In some embodiments, the plurality of auxiliary signals may correspond to the same location in the k-space.

In some embodiments, to obtain the point spread function corresponding to the wave encoding gradient, the one or more processors may generate a first image based on a first set of k-space data, wherein the first set of k-space data is obtained without applying the wave encoding gradient to the ROI. The one or more processors may generate a second image based on a second set of k-space data, wherein the second set of k-space data may be obtained by applying the wave encoding gradient to the ROI. The first set of k-space data and the second set of k-space data may correspond to the same region in the k-space. The one or more processors may determine the point spread function based on the first image and the second image.

In some embodiments, the temporal information may include at least one temporal basis function relating to the at least one temporal dimension, and the spatial information may include at least one spatial basis function relating to the at least one spatial dimension.

In some embodiments, the at least temporal dimension may include at least one of a cardiac motion, a respiratory motion, a T1 relaxation, a T2 relaxation, a chemical exchange saturation transfer (CEST), a contrast agent dynamic, a T1ρ contrast, a molecular diffusion, or an elapsed time.

In some embodiments, to determine, based on the plurality of auxiliary signals, the plurality of imaging signals, and the point spread function, the spatial information relating to the spatial dimension of the ROI, the one or more processors may construct a target function based on the plurality of imaging signals, the temporal information, and the point spread function. The one or more processors may determine the spatial information by solving the target function.

In some embodiments, to determine the spatial information by solving the target function, the one or more processors may determine estimated spatial information. The one or more processors may determine estimated imaging data based on the estimated spatial information, the point spread function, and the temporal information. The point spread function may be configured to make the estimated imaging data involve an effect of the wave encoding gradient. The one or more processors may determine a difference between the plurality of imaging signals and the estimated imaging data. The one or more processors may determine the spatial information by solving, based on the difference, the target function.

In some embodiments, the target function may include a comparison item configured to limit the difference between the plurality of imaging signals and the estimated imaging data, and a regularization item configured to limit the estimated spatial information. The comparison item may include the point spread function.

In some embodiments, the first direction and the second direction may be vertical to a readout direction.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for generating at least one target image according to some embodiments of the present disclosure;

DETAILED DESCRIPTION

Figure 1:
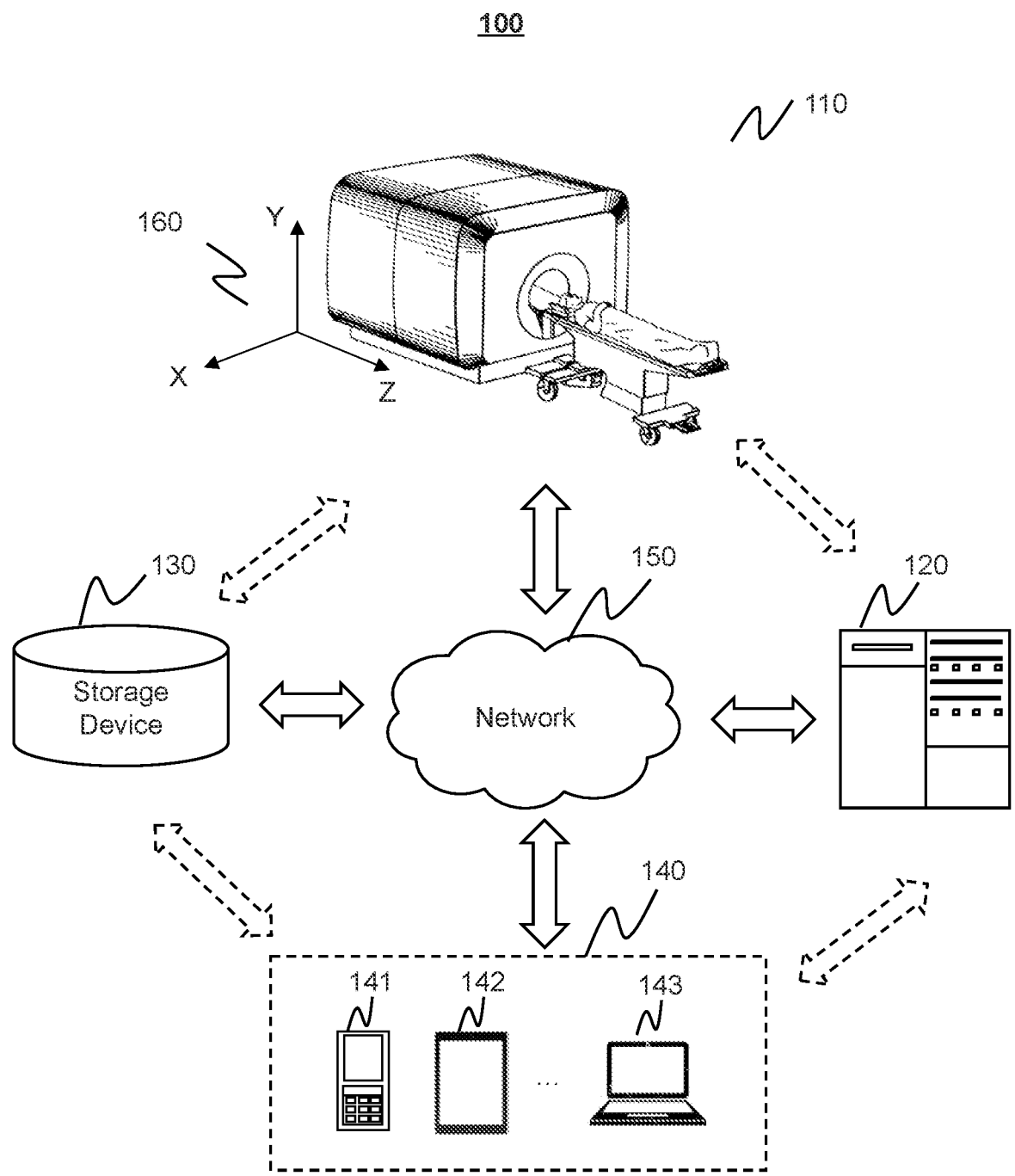
FIG. 1 is a schematic diagram illustrating an exemplary MRI system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

The term "pixel" and "voxel" in the present disclosure are used interchangeably to refer to an element in an image. The term "image" in the present disclosure is used to refer to images of various forms, including a 2-dimensional image, a 3-dimensional image, a 4-dimensional image, etc.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system. Exemplary MRI systems may include a superconducting magnetic resonance imaging system, a non-superconducting magnetic resonance imaging system, etc. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), image-guide radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

An aspect of the present disclosure relates to systems and methods for MRI, more particular, to systems and methods for MRI that combines the wave encoding technique and the multitasking technique.

MRI is an imaging technique used in radiology to capture images of an anatomy or a physiological process of a subject (e.g., a patient, or a body part thereof). MRI is based on the phenomenon of a nuclear magnetic resonance (NMR). In a typical MRI scan, a subject may be placed inside a strong static main magnetic field. MR signals may be generated by applying an RF pulse to excite the spin of the atomic nucleus in the subject. Following the excitation, the subject may emit a decaying RF signal that can be detected in the form of radiofrequency voltage in a receiver coil. In order to distinguish the received signals from different spatial positions, additional magnetic field gradients may be superimposed on the main magnetic field so that the field strength varies with spatial position, allowing the origins of MR signals emitted from the subject to be localized. According to a gradient encoding, a Fourier imaging may be performed, in which measurements representing the spatial frequency of the subject, termed as k-space, can be acquired using a specific sampling pattern, e.g., a Cartesian sampling pattern. An image reconstruction is performed by applying an inverse Fourier transform (e.g., inverse fast Fourier transform) on k-space data. However, Fourier imaging is the relatively slow in terms of its data acquisition speed, in which only limited k-space positions can be encoded per unit time and this process has to be sequentially repeated until the entire k-space region for the target spatial resolution is sampled. Such a low imaging speed not only increases patient discomfort, but also imposes limits on spatiotemporal resolution and volumetric coverage.

An alternative approach to increase the imaging speed in MRI is to accelerate MR data acquisition by collecting fewer phase-encoding lines in the k-space. A variety of parallel imaging techniques, such as a simultaneous acquisition of spatial harmonics (SMASH), a sensitivity encoding (SENSE), and a generalized autocalibrating partially parallel acquisition (GRAPPA), have been employed to accelerate the data acquisition in MRI using an array of receiving coils with spatially-varying sensitivities. MR data may be acquired using an array of independent receiver channels. A receiving coil may be more sensitive to a specific volume of tissue closer to the receiving coil, which means that the receiving coils may provide an additional source of spatial information for image reconstruction. The k-space data may be undersampled in the phase encoding direction (and potentially also the slice-encoding direction in 3D imaging) to reduce the scan time. However, the acceleration in parallel imaging may be limited by noise amplification in the reconstruction, which may increase non-linearly with an increase in the acceleration factor.

To address the above issues, a wave encoding technique is provided. In the wave encoding technique, an additional wave encoding gradient is provided by simultaneously applying, during the readout of k-space, a first oscillating gradient and a second oscillating encoding gradient (with a phase difference between the two oscillating gradients) along two directions orthogonal to the readout direction. The wave encoding technique may result in a highly efficient k-space sampling pattern that spreads aliasing evenly throughout k-space by modifying the k-space phase and slice encoding strategy, thereby improving the ability to separate the aliased signals. In this manner, the so-called g-factor penalty for parallel image reconstruction can be reduced, thereby enabling highly accelerated imaging with low artifact and negligible signal-to-noise ratio (SNR) penalties.

The multitasking technique allows acquiring MR data of a subject relating to multiple time dimensions, that is, achieving multiple tasks, via a single MRI scan of the subject. The multitasking technique may be used to conceptualize different sources of motion, relaxation, and other dynamics as different time dimensions and resolve the multiple time dimensions. By capturing, instead of avoiding the motion, relaxation, and other dynamics, the multitasking technique may efficiently perform quantitative measurement on the subject without using Electrocardiography (ECG) triggering, breath holds, etc. For example, the multitasking technique may enable non-ECG and free-breathing T1 mapping, non-ECG and free-breathing T2 mapping, and non-ECG and time-resolved T1 mapping for myocardial perfusion and dynamic contrast enhancement imaging. In other words, the multitasking technique may provide a more efficient, reliable, and comfortable imaging method for solving long-standing problems in MRI.

The present disclosure provides systems and methods for MRI that combines the wave encoding technique and the multitasking technique to combine the benefits of the multitasking technique and the wave encoding technique. Specifically, in the multitasking technique, a plurality of imaging signals and a plurality of auxiliary signals of a region of interest (ROI) of a subject (e.g., a patient) may be obtained. Temporal information of the ROI relating to at least one temporal dimension (e.g., a cardiac motion, a respiratory motion, a T1 relaxation, a T2 relaxation, a chemical exchange saturation transfer (CEST), a contrast agent dynamic, a T1ρ contrast, a molecular diffusion, an elapsed time, etc.) of the ROI may be determined based on the auxiliary signals. Spatial information of the ROI relating to at least one spatial dimension of the ROI (e.g., at least one of the x, y, and Z directions in FIG. 1) may be determined based on the temporal information and the imaging signals. At least one target image of the ROI corresponding to the spatial dimension and the at least one temporal dimensions may be generated based on the spatial information and the temporal information.

In order to combine the wave encoding technique and the multitasking technique, the imaging signals may be obtained based on the wave encoding technique. Specifically, the imaging signals may be collected by additionally applying a wave encoding gradient to the ROI. The wave encoding gradient may include a first oscillating encoding gradient in a slice encoding direction (also referred to as slice selection direction) and a second oscillating encoding gradient in a phase encoding direction. The first oscillating encoding gradient and the second oscillating encoding gradient may be applied simultaneously during the sampling of MR data and result in a corkscrew sampling pattern in k-space.

In this case, the process for determining the spatial information may be modified to adapt to the wave encoding technique. Specifically, since the spatial information may be determined based on the imaging signals acquired by the wave encoding technique, a point spread function may be introduced into the process for determining the spatial information to offset the effect the wave encoding gradient in the imaging signals. The point spread function may be used to characterize the effect of the wave encoding gradient. For example, the point spread function may characterize a point (voxel or pixel) spreading effect over the whole field of view (FOV) of a reconstructed image caused by the wave encoding gradient. The introduction of the point spread function into the process for determining the spatial information may be the key to combining the wave encoding technique and the multitasking technique.

The present disclosure provides an MRI technique that combines the advantages of both the wave encoding technique and the multitasking technique, for example, can be used to track dynamics of multiple dimensions with improved scanning efficiency. Compared to the multitasking technique, the MRI technique of the present disclosure can shorten the scanning time and/or improve the accuracy of the dynamic tracking.

FIG. 1 is a schematic diagram illustrating an exemplary MRI system according to some embodiments of the present disclosure. As illustrated, an MRI system 100 may include an MRI device 110, a processing device 120, a storage device 130, a terminal 140, and a network 150. The components of the MRI system 100 may be connected in one or more of various ways. Merely by way of example, as illustrated in FIG. 1, the MRI device 110 may be connected to the processing device 120 directly as indicated by the bi-directional arrow in dotted lines linking the MRI device 110 and the processing device 120, or through the network 150. As another example, the storage device 130 may be connected to the MRI device 110 directly as indicated by the bi-directional arrow in dotted lines linking the MRI device 110 and the storage device 130, or through the network 150. As still another example, the terminal 140 may be connected to the processing device 120 directly as indicated by the bi-directional arrow in dotted lines linking the terminal 140 and the processing device 120, or through the network 150.

The MRI device 110 may be configured to scan a subject (or a part of the subject) to acquire image data, such as echo signals (also referred to as magnetic resonance (MR) data or MR signals) associated with the subject. For example, the MRI device 110 may detect a plurality of echo signals by applying an MRI pulse sequence on the subject. In some embodiments, the MRI device 110 may include, for example, a main magnet, a gradient coil (or also referred to as a spatial encoding coil), a radio frequency (RF) coil, etc., as described in connection with FIG. 2. In some embodiments, the MRI device 110 may be a permanent magnet MRI scanner, a superconducting electromagnet MRI scanner, a resistive electromagnet MRI scanner, etc., according to types of the main magnet. In some embodiments, the MRI device 110 may be a high-field MRI scanner, a mid-field MRI scanner, a low-field MRI scanner, etc., according to the intensity of the magnetic field.

The subject scanned by the MRI device 110 may be biological or non-biological. For example, the subject may include a patient, a man-made object, etc. As another example, the subject may include a specific portion, an organ, tissue, and/or a physical point of the patient. Merely by way of example, the subject may include the head, the brain, the neck, a body, a shoulder, an arm, the thorax, the heart, the stomach, a blood vessel, soft tissue, a knee, a foot, or the like, or any combination thereof.

For illustration purposes, a coordinate system 160 including an X-axis, a Y-axis, and a Z-axis may be provided in FIG. 1. The X-axis and the Z axis shown in FIG. 1 may be horizontal, and the Y-axis may be vertical. As illustrated, the positive X direction along the X-axis may be from the right side to the left side of the MRI device 110 seen from the direction facing the front of the MRI device 110; the positive Y direction along the Y-axis shown in FIG. 1 may be from the lower part to the upper part of the MRI device 110; the positive Z direction along the Z-axis shown in FIG. 1 may refer to a direction in which the subject is moved out of a detection region (or referred to as a bore) of the MRI device 110.

In some embodiments, the MRI device 110 may be directed to select an anatomical region (e.g., a slice or a volume) of the subject along a slice selection direction and scan the anatomical region to acquire a plurality of echo signals from the anatomical region. During the scan, spatial encoding within the anatomical region may be implemented by spatial encoding coils (e.g., an X coil, a Y coil, a Z coil) along a frequency encoding direction, a phase encoding direction, and a slice selection direction. The echo signals may be sampled and the corresponding sampled data may be stored into a k-space matrix for image reconstruction. For illustration purposes, the slice selection direction herein may correspond to the Z direction defined by the coordinate system 160 and a Kz direction in k-space; the phase encoding direction may correspond to the Y direction defined by the coordinate system 160 and a Ky direction in k-space; and the frequency encoding direction (also referred to as readout direction) may correspond to the X direction defined by the coordinate system 160 and a Kx direction in k-space. It should be noted that the slice selection direction, the phase encoding direction, and the frequency encoding direction may be modified according to actual needs, and the modification may do not depart the scope of the present disclosure. More description of the MRI device 110 may be found elsewhere in the present disclosure. See, e.g., FIG. 2 and the description thereof.

The processing device 120 may process data and/or information obtained from the MRI device 110, the storage device 130, and/or the terminal(s) 140. For example, the processing device 120 may obtain a plurality of imaging signals collected by applying a wave encoding gradient to a region of interest (ROI) of a subject. The processing device 120 may obtain a plurality of auxiliary signals associated with the ROI. The processing device 120 may obtain a point spread function corresponding to the wave encoding gradient. The processing device 120 may determine, based on the plurality of auxiliary signals, temporal information relating to at least one temporal dimension of the ROI. The processing device 120 may determine, based on the plurality of auxiliary signals, the plurality of imaging signals, and the point spread function, spatial information relating to at least one spatial dimension of the ROI. The processing device 120 may generate at least one target image of the ROI based on the temporal information and the spatial information. In some embodiments, the processing device 120 may be a single server or a server group. The server group may be centralized or distributed. In some embodiments, the processing device 120 may be local or remote. For example, the processing device 120 may access information and/or data from the MRI device 110, the storage device 130, and/or the terminal(s) 140 via the network 150. As another example, the processing device 120 may be directly connected to the MRI device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the MRI device 110.

The storage device 130 may store data, instructions, and/or any other information. In some embodiments, the storage device 130 may store data obtained from the MRI device 110, the processing device 120, and/or the terminal(s) 140. The data may include image data acquired by the processing device 120, algorithms and/or models for processing the image data, etc. For example, the storage device 130 may store k-space data obtained from an MRI device (e.g., the MRI device 110). As another example, the storage device 130 may store information of a coil sensitivity of each of a plurality of coils. As still another example, the storage device 130 may store a point spread function determined by the processing device 120. As still another example, the storage device 130 may store an objective function determined by the processing device 120. As still another example, the storage device 130 may store a target image determined by the processing device 120. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the MRI system 100 (e.g., the processing device 120, the terminal(s) 140). One or more components in the MRI system 100 may access the data or instructions stored in the storage device 130 via the network 150. In some embodiments, the storage device 130 may be integrated into the MRI device 110 or the processing device 120.

The terminal(s) 140 may be connected to and/or communicate with the MRI device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the MRI system 100. In some embodiments, one or more components of the MRI system 100 (e.g., the MRI device 110, the processing device 120, the storage device 130, the terminal(s) 140, etc.) may communicate information and/or data with one or more other components of the MRI system 100 via the network 150. For example, the processing device 120 and/or the terminal 140 may obtain a plurality of target sets of k-space data from the MRI device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the MRI system 100 may include one or more additional components and/or one or more components described above may be omitted. Additionally or alternatively, two or more components of the MRI system 100 may be integrated into a single component. For example, the processing device 120 may be integrated into the MRI device 110. As another example, a component of the MRI system 100 may be replaced by another component that can implement the functions of the component. As still another example, the processing device 120 and the terminal 140 may be integrated into a single device.

Figure 2:
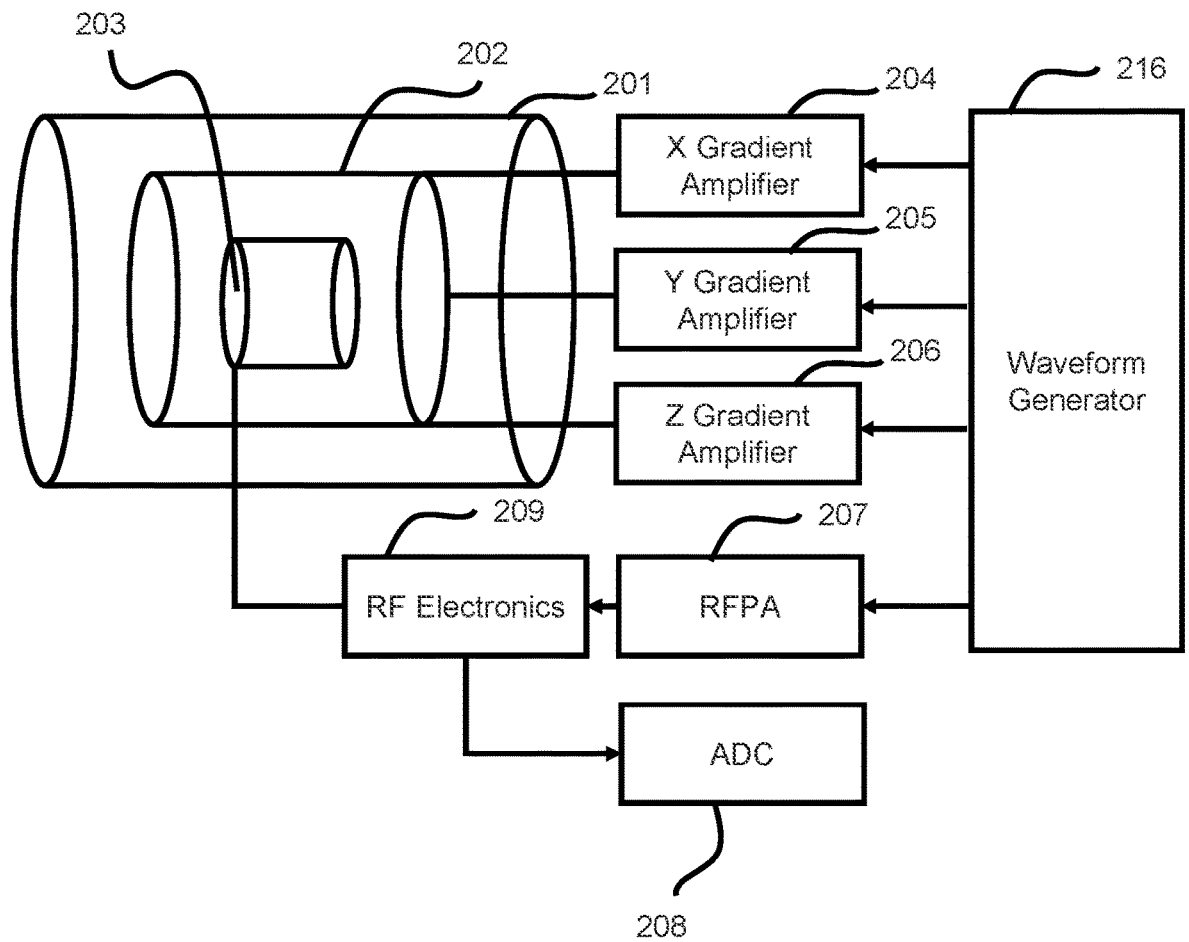
FIG. 2 is a schematic diagram illustrating an exemplary MRI device according to some embodiments of the present disclosure.

FIG. 2 is a schematic diagram illustrating an exemplary MRI device 110 according to some embodiments of the present disclosure. As illustrated, a main magnet 201 may generate a first magnetic field (or referred to as a main magnetic field) that may be applied to an object (also referred to as a subject) positioned inside the first magnetic field. The main magnet 201 may include a resistive magnet or a superconductive magnet that both need a power supply (not shown in FIG. 2) for operation. Alternatively, the main magnet 201 may include a permanent magnet. The main magnet 201 may form a detection region and surround, along the Z direction, the object that is moved into or positioned within the detection region. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. For example, the gradient coils 202 may be located in the detection region. The gradient coils 202 may surround, along the Z direction, the object that is moved into or positioned within the detection region. The gradient coils 202 may be surrounded by the main magnet 201 around the Z direction, and be closer to the object than the main magnet 201. The gradient coils 202 may generate a second magnetic field (or referred to as a gradient field, including gradient fields Gx, Gy, and Gz). The second magnetic field may be superimposed on the main magnetic field generated by the main magnet 201 and distort the main magnetic field so that the magnetic orientations of the protons of an object may vary as a function of their positions inside the gradient field, thereby encoding spatial information into MR signals generated by the region of the object being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of MR signals for image reconstruction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. For example, the RF coils 203 may be located in the detection region. The RF coils 203 may surround, along the Z direction, the object that is moved into or positioned within the detection region. The RF coils 203 may be surrounded by the main magnet 201 and/or the gradient coils 202 around the Z direction, and be closer to the object than the gradient coils 202. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate MR signals related to the region of the object being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting MR signals (e.g., echoes). After excitation, the MR signals generated by the object may be sensed by the RF coils 203. The receive amplifier then may receive the sensed MR signals from the RF coils 203, amplify the sensed MR signals, and provide the amplified MR signals to the ADC 208. The ADC 208 may transform the MR signals from analog signals to digital signals. The digital MR signals then may be sent to the processing device 140 for sampling.

In some embodiments, the main magnet coil 201, the gradient coils 202, and the RF coils 203 may be circumferentially positioned with respect to the object around the Z direction. It is understood by those skilled in the art that the main magnet 201, the gradient coils 202, and the RF coils 203 may be situated in a variety of configurations around the object.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the MRI device 110 may further include a subject positioning system (not shown). The subject positioning system may include a subject cradle and a transport device. The subject may be placed on the subject cradle and be positioned by the transport device within the bore of the main magnet 201.

MRI systems (e.g., the MRI system 100 disclosed in the present disclosure) may be commonly used to obtain an interior image from a patient for a particular region of interest (ROI) that can be used for the purposes of, e.g., diagnosis, treatment, or the like, or a combination thereof. MRI systems include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an echo signal. The echo signal is received and processed to form an MRI image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the X, Y, and Z directions, having a particular timing, frequency, and phase, may be superimposed on the uniform magnetic field such that the RF excitation signal excites the H atoms in a desired slice of the patient's body, and unique phase and frequency information is encoded in the echo signal depending on the location of the H atoms in the "image slice." Based on a gradient encoding, a Fourier imaging may be performed, in which measurements representing the spatial frequency of the subject, termed as k-space, can be acquired using a specific sampling trajectory. The specific sampling trajectory may include a Cartesian trajectory or a non-Cartesian trajectory such as a spiral trajectory, a radial trajectory, etc., and an image reconstruction is performed by applying an inverse Fourier transform (e.g., inverse fast Fourier transform) on k-space data.

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequences may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. For each MRI scan, the resulting echo signals may be digitized and processed to reconstruct an image in accordance with the MRI imaging protocol that is used.

Figure 3:
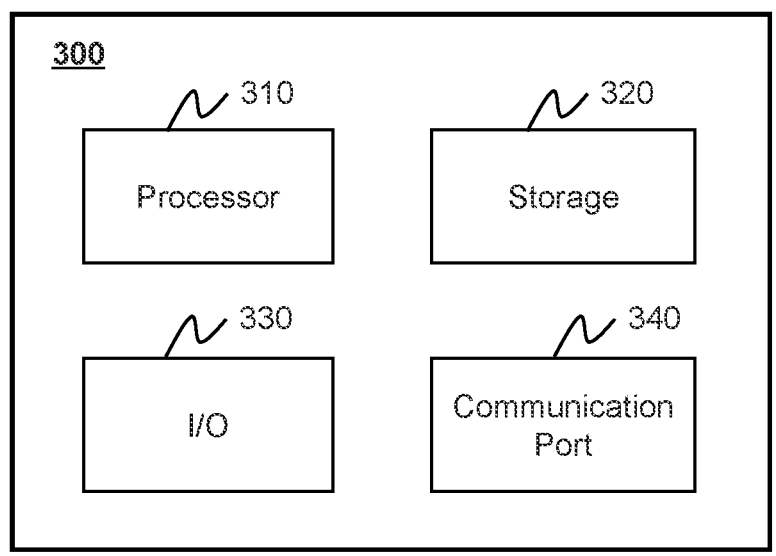
FIG. 3 is a schematic diagram illustrating exemplary hardware and/or software components of a computing device according to some embodiments of the present disclosure.

FIG. 3 is a schematic diagram illustrating exemplary hardware and/or software components of a computing device 300 according to some embodiments of the present disclosure. In some embodiments, one or more components of the MRI system 100 may be implemented on one or more components of the computing device 300. Merely by way of example, the processing device 120 and/or the terminal(s) 140 may be implemented one or more components of the computing device 300, respectively.

As illustrated in FIG. 3, the computing device 300 may include a processor 310, a storage device 320, an input/output (I/O) 330, and a communication port 340. The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process image data of a subject obtained from the MRI device 110, the storage device 130, terminal(s) 140, and/or any other component of the MRI system 100.

In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage device 320 may store data/information obtained from the MRI device 110, the storage device 130, the terminal(s) 140, and/or any other component of the MRI system 100. In some embodiments, the storage device 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random-access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 320 may store one or more programs and/or instructions to perform exemplary methods described in the present disclosure.

The I/O 330 may input and/or output signals, data, information, etc. In some embodiments, the I/O 330 may enable a user interaction with the computing device 300 (e.g., the processing device 120). In some embodiments, the I/O 330 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The communication port 340 may be connected to a network (e.g., the network 150) to facilitate data communications. The communication port 340 may establish connections between the computing device 300 (e.g., the processing device 120) and one or more components of the MRI system 100 (e.g., the MRI device 110, the storage device 130, and/or the terminal(s) 140). The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or any combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
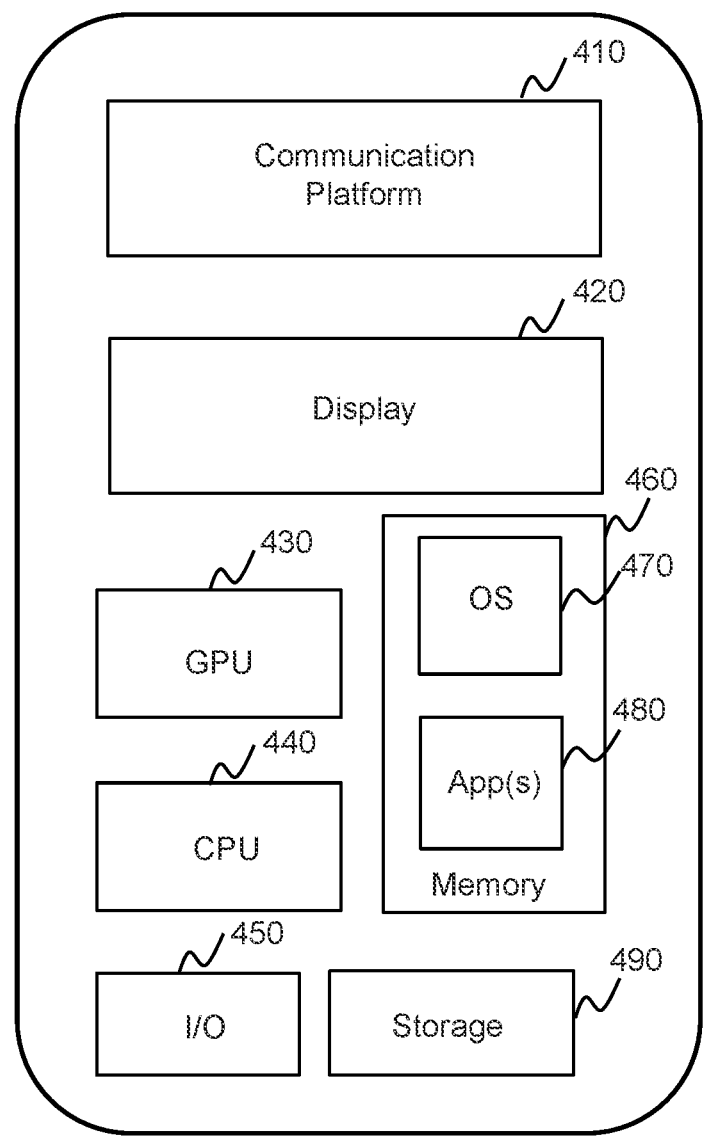
FIG. 4 is a schematic diagram illustrating exemplary hardware and/or software components of a mobile device may be implemented according to some embodiments of the present disclosure.

FIG. 4 is a schematic diagram illustrating exemplary hardware and/or software components of a mobile device 400 may be implemented according to some embodiments of the present disclosure. In some embodiments, one or more components of the MRI system 100 may be implemented on one or more components of the mobile device 400. Merely by way of example, the terminal 140 may be implemented on one or more components of the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to the MRI system 100. User interactions with the information stream may be achieved via the I/O 450 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal. A computer may also act as a server if appropriately programmed.

Figure 5:
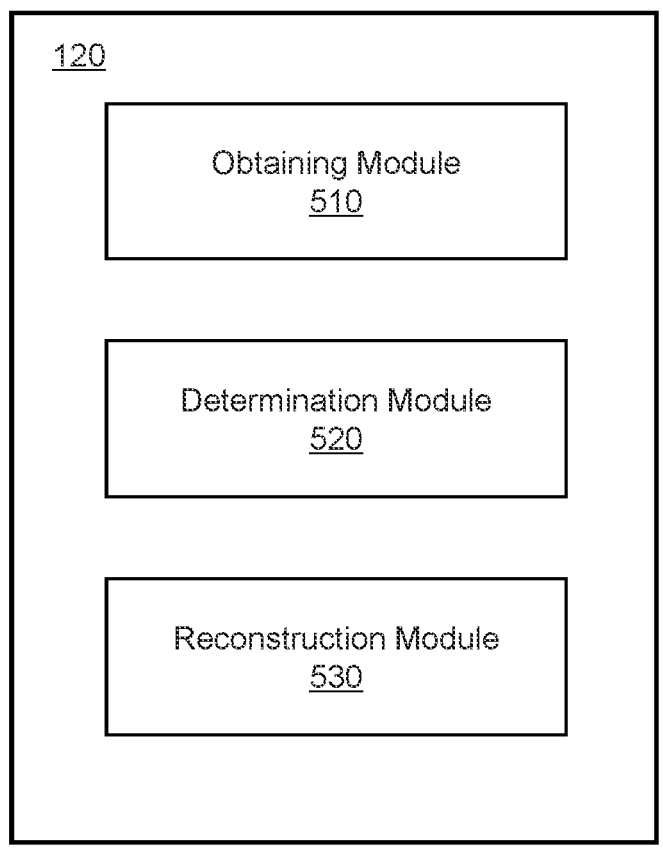
FIG. 5 is a schematic diagram illustrating an exemplary processing device according to some embodiments of the present disclosure.

FIG. 5 is a schematic diagram illustrating an exemplary processing device according to some embodiments of the present disclosure. In some embodiments, the processing device 120 may include an obtaining module 510, a determination module 520, and a reconstruction module 530. In some embodiments, the modules may be hardware circuits of all or part of the processing device 120. The modules may also be implemented as an application or set of instructions read and executed by the processing device 120. Further, the modules may be any combination of the hardware circuits and the application/instructions. For example, the modules may be part of the processing device 120 when the processing device 120 is executing the application/set of instructions.

The obtaining module 510 may obtain a plurality of imaging signals collected by applying a wave encoding gradient to a region of interest (ROI) of a subject. The wave encoding gradient may include a first oscillating encoding gradient in a first direction and a second oscillating encoding gradient in a second direction.

The obtaining module 510 may obtain a plurality of auxiliary signals (also referred to as navigator signals) associated with the ROI.

The obtaining module 510 may obtain a point spread function corresponding to the wave encoding gradient.

The determination module 520 may determine, based on the plurality of auxiliary signals, temporal information relating to at least one temporal dimension of the ROI.

The determination module 520 may determine, based on the plurality of auxiliary signals, the plurality of imaging signals, and the point spread function, spatial information relating to at least one spatial dimension of the ROI.

The reconstruction module 530 may generate one or more target images of the ROI based on the temporal information and the spatial information.

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. Two or more of the modules may be combined as a single module, and any one of the modules may be divided into two or more units. For example, the obtaining module 510 and the determination module 520 may be combined as a single module. As another example, the obtaining module 510 may be divided into two units. One of the two unit may be configured to obtain k-space data such as the imaging signals and the auxiliary signals, and the other one of the two unit may be configured to obtain the point spread function.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may further include a storage module (not shown in FIG. 5). The storage module may be configured to store data generated during any process performed by any component of in the processing device 120. As another example, each of the components of the processing device 120 may include a storage device. Additionally or alternatively, the components of the processing device 120 may share a common storage device.

FIG. 6 is a flowchart illustrating an exemplary process 600 for generating at least one target image according to some embodiments of the present disclosure. In some embodiments, the process 600 may be implemented in the MRI system 100 illustrated in FIG. 1. For example, the process 600 may be stored in the storage device 130 and/or the storage (e.g., the storage 320, the storage 490) as a form of instructions, and invoked and/or executed by the processing device 120 (e.g., the processor 310 of the computing device 300 as illustrated in FIG. 3, the CPU 440 of the mobile device 400 as illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 120 (e.g., the obtaining module 510) may obtain a plurality of imaging signals collected by applying a wave encoding gradient to a region of interest (ROI) of a subject. The wave encoding gradient may include a first oscillating encoding gradient in a first direction and a second oscillating encoding gradient in a second direction.

In some embodiments, the imaging signals may be acquired by applying a first pulse sequence to the ROI. The imaging signals may be k-space data acquired by filling MR data (e.g., one or more echoes of the ROI) received by a plurality of receiving coils (e.g., the RF coils 203) of an MRI device (e.g., the MRI device 110) into k-space along a sampling pattern. The MR data may be generated based on the first pulse sequence.

In some embodiments, the ROI may include a slab or a volume of the subject for 3D imaging. In some embodiments, the ROI may include a plurality of slices of the subject for 2D imaging, e.g., 2D SMS imaging.

The imaging signals may include high-spatial resolution image data relating to at least one spatial-varying dimension (also referred to as spatial dimension) of the ROI of the subject. Exemplary spatial-varying dimensions may relate to a slice selection direction, a phase encoding direction, a frequency encoding direction, or the like, or any combination thereof. In some embodiments, the imaging signal may be used to determine spatial information including at least one spatial basis function relating to the at least one spatial-varying dimension of the ROI, which will be described in detail in connection with operation 650.

In some embodiments, the imaging signals may include two-dimensional (2D) k-space data, three-dimensional (3D) k-space data, four-dimensional (4D) k-space data, or the like. As used herein, 4D k-space data refers to a data form containing 3D k-space data over time. Merely by way of example, the 3D imaging signals may be a 256*256*256 digital matrix.

In some embodiments, the imaging signals may be undersampled along at least one of the slice selection direction, the phase encoding direction, and the readout direction, i.e., only a part of a plurality of data points in the k-space may be obtained by sampling the first MR data, while the remaining part of the plurality of data points in the k-space may be obtained by assigning one or more values not sampled from the first MR data. For illustration purposes, the processing device 120 may assign the unsampled data points with one or more initial values, e.g., zero.

In some embodiments, the imaging signals may be acquired by the application of a wave encoding technique. The wave encoding technique may refer to an acquisition method in which an additional wave encoding gradient is applied by the simultaneous application, during the sampling of k-space, of a first oscillating encoding gradient along a first direction and a second oscillating encoding gradient along a second direction, leading to a corkscrew sampling pattern in the k-space. Details regarding the wave encoding technique may be found in the reference "Berkin Bilgic, et al., Wave-CAIPI for highly accelerated 3D imaging, Magn Reson Med. 2015 June; 73(6): 2152-2162," which is incorporated herein by reference.

In some embodiments, the first pulse sequence may include a wave encoding gradient that includes a first oscillating encoding gradient in a first direction and a second oscillating encoding gradient in a second direction.

In some embodiments, the first direction and the second direction may be vertical to a readout direction. For example, the first direction may be the slice selection direction corresponding to the Z direction defined by the coordinate system 160 in FIG. 1 and a Kz direction in k-space. The second direction may be the phase encoding direction correspond to the Y direction defined by the coordinate system 160 in FIG. 1 and a Ky direction in k-space. The first direction and the second direction may be vertical to the readout direction corresponding to the X direction defined by the coordinate system 160 in FIG. 1 and a Kx direction in k-space.

In some embodiments, the wave encoding gradient may lead to a corkscrew sampling pattern in the k-space. For example, the imaging signals may be acquired by filling the MR data into the k-space along a corkscrew sampling pattern.

In some embodiments, the first oscillating encoding gradient may be the same as or different from the second oscillating encoding gradient. In some embodiments, the first oscillating encoding gradient and/or the second oscillating encoding gradient may oscillate in a periodic way. In some embodiments, the first oscillating encoding gradient and/or the second oscillating encoding gradient may oscillate in an aperiodic way. For example, the first oscillating encoding gradient and/or the second oscillating encoding gradient may oscillate in a random way. As another example, the first oscillating encoding gradient and/or the second oscillating encoding gradient may oscillate in an aperiodic but regular way. For instance, the first (or second) oscillating encoding gradient may oscillate in a way where the amplitude of the first (or second) oscillating encoding gradient may vary (increase or decrease) gradually.

In some embodiments, the waveform of the first oscillating encoding gradient and/or the second oscillating encoding gradient may include a trapezoidal lobe, a triangular lobe, a sinusoidal lobe, a square lobe, a rectangular lobe, or the like, or any combination thereof.

In some embodiments, there may be a phase difference between the first oscillating encoding gradient and the second oscillating encoding gradient. The phase difference may affect a rotation angle of the corkscrew trajectory. In some embodiments, the phase difference may be any value, e.g., $\pi/2$, etc.

In some embodiments, the first pulse sequence may include an RF excitation pulse that is played out in the presence of a slice selection gradient in order to produce transverse magnetization in the ROI. The slice selection gradient may be applied in a first direction (e.g., the slice selection direction). Following excitation of the nuclear spins in the ROI, a spatial encoding gradient (e.g., at least one of a slice encoding gradient, a phase encoding gradient, and a readout gradient (also referred to as a frequency encoding gradient)) may be applied along at least one of the first direction, the second direction (e.g., the phase encoding direction), and the third direction (e.g., the readout direction) to spatially encode MR data of the ROI. In some embodiments, the first pulse sequence may further include a wave encoding gradient including a first oscillating encoding gradient in the first direction and a second oscillating encoding gradient in the second direction. The first oscillating encoding gradient and the second oscillating encoding gradient may be simultaneously applied during the readout of the MR data. Details regarding the first pulse sequence may be found elsewhere in the present disclosure (e.g., descriptions in connection with FIG. 7 and FIG. 8).

In some embodiments, the first pulse sequence excluding the wave encoding gradient may lead to a first sampling pattern in the k-space. The first pulse sequence including the wave encoding gradient may lead to a second sampling pattern in the k-space. The second sampling trajectory may include a corkscrew pattern around the first sampling pattern. Details regarding the first sampling pattern and the second sampling pattern may be found elsewhere in the present disclosure (e.g., descriptions in connection with FIG. 9 and FIG. 10).

In some embodiments, the sampling pattern of the imaging signals may include a uniform sampling pattern, a non-uniform sampling pattern, or the like. Exemplary non-uniform sampling pattern may include a variable density sampling pattern, a random sampling pattern. For example, the imaging signals may be obtained by filling the MR data into the k-space along a uniform corkscrew pattern, a variable density corkscrew pattern, a random corkscrew pattern, or the like.

In some embodiments, the k-space trajectory produced by the first pulse sequence may have a starting point that is defined by the waveform (e.g., the amplitude and/or polarity) of the spatial encoding gradient (e.g., the phase encoding gradient and/or the slice encoding gradient) in the first pulse sequence.

In some embodiments, the starting points may be evenly and uniformly distributed in the k-space. For example, a distance between the starting points may be the same. In this way, the plurality of corkscrew trajectories may be uniformly distributed in the k-space.

In some embodiments, the starting points may be distributed in the k-space in a random way. For example, a distance between the starting points may be different. In this way, the plurality of corkscrew trajectories may be randomly distributed in the k-space.

In some embodiments, the starting points may be distributed in the k-space with variable densities. For example, in the Ky direction and/or the Kz direction, the distribution density of the starting points may change over the k-space location. In this way, the plurality of corkscrew trajectories may be distributed in the k-space with variable densities. For example, the sampling density may satisfy a Gaussian distribution or a student distribution. The sampling density in a central k-space region may be relatively high, and the sampling density in a periphery region of the k-space may be relatively low. As another example, the sampling density may satisfy a periphery distribution, in which the sampling density in a central k-space region may be relatively low, and the sampling density in a periphery region of the k-space may be relatively high.

In some embodiments, the processing device 120 may obtain the imaging signals based on the first MR data and a mask. For example, the processing device 120 may obtain the first MR data acquired by the plurality of receiving coils of the MRI device 110. The processing device 120 may obtain a mask. Further, the processing device 120 may obtain the imaging signals based on the first MR data and the mask. In some embodiments, the mask may include a 2D matrix, a 3D matrix, or the like. Each location in the mask may correspond to a data point in the k-space. For illustration purposes, the mask may include a binary matrix (e.g., a 2D binary matrix, a 3D binary matrix), where "1" means that a corresponding data point in the k-space is sampled, and "0" means that a corresponding data point in the k-space is not sampled. In some embodiments, a plurality of masks corresponding to a plurality of sampling patterns or trajectories may be stored in a storage device (e.g., the storage device 130) of the MRI system 100. For example, the plurality of masks may include a Cartesian sampling mask, a spiral sampling mask, a radial sampling mask, a corkscrew sampling mask (e.g., a variable density corkscrew sampling mask, a uniform corkscrew sampling mask, a random corkscrew sampling mask), or the like, or any combination thereof. The processing device 120 may determine the sampling pattern or trajectory based on actual needs (e.g., a type of the MRI device, a quality requirement of a reconstructed image). The processing device 120 may select the mask corresponding to the determined sampling pattern or trajectory from the plurality of masks stored in the storage device.

More Details regarding the variable density sampling pattern may be found in, for example, U.S. application Ser. No. 17/304,652, which is incorporated herein by reference.

In some embodiments, the processing device 120 may obtain the imaging signals from one or more components (e.g., the MRI device 110, the terminal 140, and/or the storage device 130) of the MRI system 100 or an external storage device via the network 150. For example, the MRI device 110 may transmit the imaging signals to the storage device 130, or any other storage device for storage. The processing device 120 may obtain the imaging signals from the storage device 130, or any other storage device. As another example, the processing device 120 may obtain the imaging signals from the MRI device 110 directly.

In 620, the processing device 120 (e.g., the obtaining module 510) may obtain a plurality of auxiliary signals (also referred to as navigator signals) associated with the ROI.

In some embodiments, the auxiliary signals may be acquired by applying a second pulse sequence to the ROI. The auxiliary signals may be k-space data acquired by filling MR data (e.g., one or more echoes of the ROI) received by a plurality of receiving coils (e.g., the RF coils 203) of an MRI device (e.g., the MRI device 110) into k-space along a sampling pattern. The MR data may be generated based on the second pulse sequence.

In some embodiments, the auxiliary signals may include two-dimensional (2D) k-space data, three-dimensional (3D) k-space data, four-dimensional (4D) k-space data, or the like.

In some embodiments, the first pulse sequence and/or the second pulse sequence may include a spin echo (SE) sequence, a gradient echo sequence, a diffusion sequence, an inversion recovery (IR) sequence, or the like, or any combination thereof. For instance, the spin echo sequence may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequence may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. In some embodiments, the first pulse sequence may be the same as or different from the second pulse sequence.

In some embodiments, the auxiliary signals may include high-temporal resolution data relating to at least one time-varying dimension (also referred to as temporal dimension) of the ROI of the subject, which may be used to implement the multitasking technique. Exemplary time-varying dimensions may relate to a cardiac motion, a respiratory motion, a T1 relaxation, a T2 relaxation, a chemical exchange saturation transfer (CEST), a contrast agent dynamic, a T1ρ contrast, a molecular diffusion, an elapsed time, or the like, or any combination thereof. It should be noted that the exemplary time-varying dimensions are merely provided for illustration purposes, and not intended to be limiting. The at least one time-varying dimension may include any dimension that reflects time-varying characteristics or dynamic information of the subject. In some embodiments, the auxiliary signals may be used to estimate temporal information including at least one temporal basis function relating to the at least one time-varying dimension, which will be described in detail in connection with operation 640.

In some embodiments, the auxiliary signals may correspond to the same subset (e.g., same location) of k-space and collected by sampling the subset of k-space repeatedly with a high sampling frequency. For example, the auxiliary signals may correspond to one or more same k-space lines (e.g., a k-space line of Ky=Kz=0 in 3D k-space, or Ky=0 in 2D k-space) in k-space and be acquired by sampling the k-space line repeatedly with a high sampling frequency. As another example, the auxiliary signals may correspond to the central region of k-space and be acquired by sampling the central region of k-space line repeatedly with a high sampling frequency. In some embodiments, the central region may be determined according to actual needs or experience. For example, taking the center point (e.g., a point of Kx=Ky=Kz=0 in 3D k-space, or Kx=Ky=0 in 2D k-space) of k-space as the origin, the region of k-space in which the frequency value is from 0 to 120 Hz may be determined as the central region. It can be understood that the frequency corresponding to the central region of the k-space may be lower than a frequency threshold.

As used herein, a high sampling frequency refers to a sampling frequency that is higher than a threshold frequency. The threshold frequency may be a default value, or determined manual by a user, or determined by the processing device 120 according to data analysis. For example, the threshold frequency may be determined according to the at least one time-varying dimension to be analyzed. Merely by way of example, a time-varying dimension may relate to the respiratory motion of the subject, and the respiration cycle of the subject is close to 0.75 seconds (s). In order to capture dynamic information relating to the respiratory motion of the subject, the sampling frequency may need to be greater than a threshold frequency of 1/0.75 Hertz (HZ). As another example, the threshold frequency may be determined according to actual requirements (e.g., the accuracy requirement), experience, a data model, etc.

In some embodiments, the sampling pattern of the imaging signals may be the same as or different from the sampling pattern of the auxiliary signals. In some embodiments, the auxiliary signals may be acquired using or without the wave encoding technique. For example, a first pulse sequence including a wave encoding gradient may be applied to the ROI so as to acquire the imaging signals based on the corkscrew sampling pattern 1000 in FIG. 10, and a second pulse sequence including the same wave encoding gradient may be applied to the ROI so as to acquire the auxiliary signals based on a corkscrew sampling trajectory along the Kx direction. Alternatively, a second pulse sequence including a different wave encoding gradient may be applied to the ROI so as to acquire the auxiliary signals based on a different corkscrew sampling trajectory along the Kx direction. Alternatively, a second pulse sequence including a wave encoding gradient may be applied to the ROI so as to acquire the auxiliary signals based on a corkscrew sampling trajectory along a direction different from the Kx direction. Alternatively, a second pulse sequence without a wave encoding gradient may be applied to the ROI so as to acquire the auxiliary signals based on a sampling trajectory that is not in the shape of corkscrew, e.g., a Cartesian sampling trajectory, a radial sampling trajectory, a spiral sampling trajectory, a zigzag sampling trajectory, a propeller sampling trajectory, or the like.

In some embodiments, the auxiliary signals and the imaging signals may be acquired in any sampling order during the MRI scan of the subject. In some embodiments, the auxiliary signals and the imaging signals may be acquired interleaved during the MRI scan of the subject. For example, the auxiliary signals may be acquired by repeatedly sampling the same location of the k-space. Every sampling of the same location of the k-space may be performed before, after, or during the sampling of a first count (e.g., 1, 2, 3, 5, 10, etc.) of corkscrew trajectories like the corkscrew trajectory 1010 in the sampling pattern 1000.

In some embodiments, the first count may be set according to actual requirements, for example, a sampling frequency of the auxiliary signals needs to be greater than the threshold frequency and/or enough imaging signals need to be acquired for image reconstruction.

In 630, the processing device 120 (e.g., the obtaining module 510) may obtain a point spread function corresponding to the wave encoding gradient.

Figure 9:
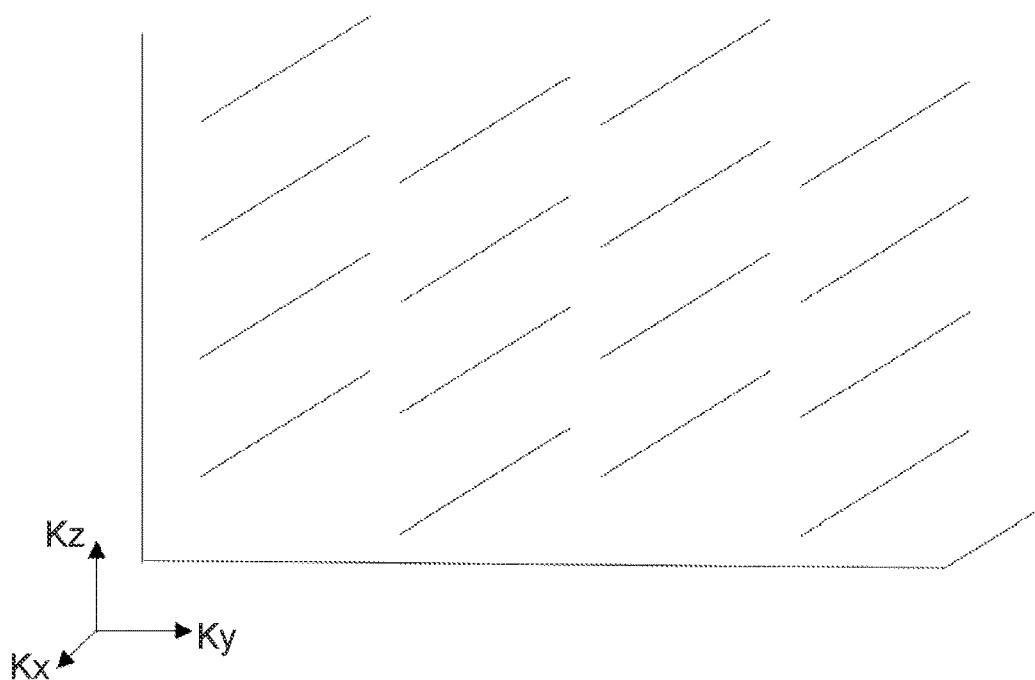
FIG. 9 is a schematic diagram illustrating an exemplary Cartesian sampling pattern according to some embodiments of the present disclosure.

For illustration purposes, for rectilinear (Cartesian) 3D imaging with phase and partition encoding (i.e., the slice selection encoding), e.g., sampling based on the sampling pattern 900 in FIG. 9, the received signals may be expressed using the k-space notation at fixed Ky and Kz as Equation (1):

$$s(t) = \int_{x,y,z} m(x,y,z) e^{-i2\pi[k_x(t)x + k_y y + k_z z]} dxdydz, \quad (1)$$

where m(x, y, z) refers to an underlying image (i.e., a reconstructed image); Kx refers to a readout encoding; Ky refers to a phase encoding; and Kz refers to a slice selection encoding.

When an additional wave encoding gradient including a first oscillating encoding gradient $g_z$ in the slice selection direction (e.g., the Z direction) and a second oscillating encoding gradient $g_y$ in the phase encoding direction (e.g., the Y direction) is applied during each readout line, the received signals (e.g., the imaging signals) may be expressed as Equation (2):

$$s(t)=\int_{x,y,z}m(x,y,z)\exp\{-i\gamma\int_0^t[g_y(\tau)y+g_z(\tau)z]d\tau\}dxdydz, \quad (2)$$

In some embodiments, Equation (2) may be rewritten more succinctly as Equation (3):

$$\text{wave}[x,y,z]=F_x^{-1}Psf[k,y,z](F_xm[x,y,z]), \quad (3)$$

where wave[x, y, z] refers to an image acquired with the wave encoding gradient; Fx refers to a discrete Fourier transform (DFT) operation in the X direction; $F_x^{-1}$ refers to an inverse DFT operation in the X direction; k refers to a k-space index that enumerates the data points acquired per readout line; and Psf[k, y, z] refers to a point spread function (PSF) that describes the effect of the wave encoding gradient: each readout line in the underlying image m[x, y, z] is convolved with the PSF to yield the acquired wave image wave[x,y,z], or a multiplication of the sampled k-space and the PSF along the X direction to yield the wave encoded k-space data, in which the PSF is a function of spatial location (y, z).

In some embodiments, the point spread function may be used to characterize the effect of the wave encoding gradient in the wave encoding technique as described in connection with operation 610. For example, the point spread function may characterize a point (voxel or pixel) spreading effect over the whole field of view (FOV) of a reconstructed image caused by the corkscrew sampling pattern.

In some embodiments, the processing device 120 may generate a first image based on a first set of k-space data. The first set of k-space data may be obtained without applying the wave encoding gradient to the ROI. The processing device 120 may generate a second image based on a second set of k-space data. The second set of k-space data may be obtained by applying the wave encoding gradient to the ROI. The first set of k-space data and the second set of k-space data may correspond to the same region in the k-space. The processing device 120 may determine the point spread function based on the first image and the second image.

In some embodiments, the first set of k-space data may be obtained by sampling a subset of the k-space (e.g., the central region of the k-space) based on the first pulse sequence excluding the wave encoding gradient to the ROI. The second set of k-space data may be obtained by sampling the same subset of the k-space based on the first pulse sequence including the wave encoding gradient to the ROI.

In some embodiments, the processing device 120 may generate the first image and the second image based on one or more image reconstruction techniques. Exemplary reconstruction techniques may include Fourier reconstruction, inverse Fourier reconstruction, constrained image reconstruction, regularized image reconstruction in parallel MRI, compressed-sensing (CS)-parallel imaging (PI) reconstruction, or the like, or any combination thereof. Exemplary CS-PI reconstruction techniques may include sparse sensitivity encoding (SENSE), l1-iterative self-consistent parallel imaging reconstruction (SPIRIT), CS-SENSE, CS-generalized autocalibrating partially parallel acquisitions (GRAPPA), or the like, or any combination thereof.

In some embodiments, the processing device 120 may determine the point spread function based on the division between the first image and the second image.

In some embodiments, each pixel (or voxel) in an MRI image (e.g., the first image, the second image) may include phase information and magnitude information reflecting an interaction between the subject and magnetic fields generated by the MRI device. The processing device 120 may determine the point spread function based on phase information associated with the first image and the second image. In some embodiments, the processing device 120 may determine a phase difference between the first image and the second image as the point spread function. For example, the processing device 120 may determine a first phase matrix of the first image based on values of pixels (or voxels) in the first image. A value in the first phase matrix of the first image may be a phase value of a corresponding pixel (or voxel) in the first image. The processing device 120 may determine a second phase matrix of the second image based on values of pixels (or voxels) in the second image. A value in the second phase matrix of the second image may be a phase value of a corresponding pixel (or voxel) in the second image. The processing device 120 may determine a phase difference matrix between the first phase matrix of the first image and the second phase matrix of the second image as the point spread function. For example, the processing device 120 may determine the phase difference matrix by determining a ratio between the first phase matrix of the first image and the second phase matrix of the second image.

In some embodiments, under the premise that operation 630 is performed before operation 650, the performing order of operation 630 relative to operations 610, 620, and 640 may be any order.

In 640, the processing device 120 (e.g., the determination module 520) may determine, based on the plurality of auxiliary signals, temporal information relating to at least one temporal dimension of the ROI.

In some embodiments, a target image of the ROI with multiple dimensions (e.g., at least one spatial-varying dimension and at least one time-varying dimension) may be represented by a multi-dimensional tensor. For example, the target image may be represented as an (N+1)-way image tensor (or array), wherein the first tensor dimension may index the at least one spatial-varying dimension and each of the other N tensor dimension(s) may index a time-varying dimension. N is a positive integer and equal to the count of the time-varying dimension(s).

A low-rank tensor image model may be used to resolve multiple overlapping dynamics (e.g., the at least one time-varying dimension). For example, according to the low-rank tensor image model, the target image may be expressed by a product of a core tensor and (N+1) basis matrices. The core tensor may govern the interaction between the (N+1) basis matrices. The (N+1) basis matrices may include a spatial factor matrix and N temporal factor matrix (or matrices). The spatial factor matrix may include one or more spatial basis functions relating to the at least one spatial-varying dimension of the ROI. Each of the N temporal factor matrix (or matrices) may correspond to one of the at least one time-varying dimension and include one or more temporal basis functions relating to the corresponding time-varying dimension. In order to generate the target image, the at least one spatial basis function, the at least one temporal basis function, and the core tensor may need to be determined based on the auxiliary signals and the imaging signals.

In some embodiments, the temporal information may include one or more temporal basis functions relating to the at least one time-varying dimension. For example, the one or more temporal basis functions may include one or more cardiac temporal basis functions relating to the cardiac motion of the ROI, one or more respiratory temporal basis functions relating to the respiratory motion of the ROI, one or more T1 recovery temporal basis functions relating to the T1 relaxation of the ROI, or the like, or any combination thereof. A temporal basis function relating to a time-varying dimension may reflect dynamic information along the time-varying dimension and include high-temporal resolution information.

In some embodiments, the processing device 120 may determine the one or more temporal basis functions of the one or more time-varying dimensions and the core tensor based on the auxiliary signals obtained in operation 620.

As illustrated in operation 620, the auxiliary signals may be acquired by repeatedly sampling a subset of k-space. Therefore, the auxiliary signals may correspond to a partially encoded image relating to the one or more time-varying dimensions of the ROI. Therefore, the auxiliary signals may include the temporal information of the ROI, and the temporal information may be extracted from the auxiliary signals.

For example, the processing device 120 may construct a first optimization function (also referred to as a first objective function or a first target function) relating to under-sampled auxiliary data (e.g., the auxiliary signals obtained in operation 620), a low-rank tensor representing full-sampled auxiliary signals to be determined, and a matrix corresponding to each time-varying dimension. The matrix corresponding to a time-varying dimension may include rows indexing the time-varying dimension and columns indexing the other time-varying dimension(s). The processing device 120 may determine the low-rank tensor representing the full-sampled auxiliary signals by solving the first optimization function.

According to the low-rank tensor, the processing device 120 may determine the at least one temporal basis function for each time-varying dimension and the core tensor. The low-rank tensor may be decomposed into a partially encoded spatial factor matrix, a core tensor, and one or more temporal basis matrices. For example, the processing device 120 may utilize an explicit strategy to recover the one or more temporal basis functions and the core tensor based on the low-rank tensor according to a singular value decomposition (SVD) algorithm or a higher order singular value decomposition (HOSVD) algorithm.

In 650, the processing device 120 (e.g., the determination module 520) may determine, based on the plurality of auxiliary signals, the plurality of imaging signals, and the point spread function, spatial information relating to at least one spatial dimension of the ROI.

In some embodiments, the spatial information may include a spatial factor matrix that includes one or more spatial basis functions relating to the at least one spatial-varying dimension of the ROI.

A spatial basis function may include high-spatial resolution information along the spatial-varying dimension(s). For example, the spatial basis function may reflect a relationship between pixel information of the ROI in the image domain and spatial information of the ROI in the physical domain. In some embodiments, the spatial basis function may be represented as a basis image that includes high-spatial resolution information. Different spatial basis functions may be represented as basis images that include different high-spatial resolution information.

In some embodiments, the processing device 120 may construct a second optimization function (also referred to as a second objective function or a second target function) relating to the at least one spatial basis function. In some embodiments, the second optimization function may incorporate the imaging signals, the point spread function, and the time information. The processing device 120 may further determine the spatial information by solving the second optimization function.

In some embodiments, the processing device 120 may determine estimated spatial information. The processing device 120 may determine estimated imaging data based on the estimated spatial information, the point spread function, and the temporal information. The processing device 120 may determine a difference between the plurality of imaging signals and the estimated imaging data. The processing device 120 may determine the spatial information by solving, based on the difference, the second optimization function.

In some embodiments, the second optimization function may be solved by minimizing the difference to obtain a satisfactory condition, for example, the difference is less than a threshold. In some embodiments, the second optimization function may be solved using multiple iterations. For example, in the current iteration, in response to determining that the difference is less than the threshold, the estimated spatial information corresponding to the current iteration may be used as the spatial information of the ROI. In response to determining that the difference is not less than the threshold, new estimated spatial information may be obtained to initiate a new iteration.

In some embodiments, the second optimization function may include a comparison item configured to limit the difference between the plurality of imaging signals and the estimated imaging data. Since, the imaging signals may be wave encoded k-space data including the effect of the wave encoding gradient, the comparison item may include the point spread function to make the estimated imaging data relate to the wave encoding gradient, so as to offset the effect of the wave encoding gradient in the imaging signals.

In some embodiments, the second optimization function may further include a regularization item configured to limit the estimated spatial information. The regular term may be configured to stabilize the estimated spatial information. For example, the regular term may make the estimated spatial information obtained in the multiple iterations not fluctuate too much, which causes the spatial information finally obtained accurate. In some embodiments, the regularization term may be determined based on the estimated spatial information. For example, the L1 norm of a coefficient determined by performing wavelet transformation on the estimated spatial information may be used as the regularization term. As another example, the total variation of the spatial dimension of the estimated spatial information may be used as the regularization term. As still another example, other regularization algorithms, such as Bayesian algorithm, etc., may also be used to obtain the regularization term. In some embodiments, the regularization item may be omitted.

Merely by way of example, the processing device 120 may determine the spatial information of the ROI according to a second optimization function shown in Equation (4) as below:

$$\hat{U} = \arg\min_{U_x} \lVert d - \Omega(FPF_x SU_x \Phi) \rVert_2^2 + R(U_x), \tag{4}$$

where $\hat{U}$ represents an optimal spatial factor matrix (e.g., the spatial information to be determined) of the ROI determined by solving Equation (4), $U_x$ represents estimated spatial factor matrix (e.g., the estimated spatial information) of the ROI, d represents the imaging signals, $\Omega$ represents an undersampling operator corresponding to the imaging signals, F represents a Fourier transformation operator, S represents a coil sensitive map corresponding to the ROI, $\Phi$ represents a product of the core tensor and the one or more temporal factor matrices, P represents the point spread function (e.g., determined in operation 630) corresponding to the wave encoding gradient applied to acquire the imaging signals, R(U$_x$) represents a regularization item that is a constraint item relating to the spatial factor matrix of the ROI (which may be omitted in some conditions), and F$_x$ represents a Fourier transformation along the X direction (e.g., the readout direction). In some embodiments, the comparison item of Equation (4) may include $$\arg\min_{U_x}\|d - \Omega(FPF_xSU_x\Phi)\|_2^2.$$

In some embodiments, if the imaging signals are acquired in a varied-density way or a random way by applying a mask illustrated in operation 610, the comparison item of the second optimization function may need to incorporate the mask. For example, the mask may be incorporated into the undersampling operator $\Omega$.

In some embodiments, the processing device 120 may determine estimated imaging data based on $\Omega(FPF_xSU_x\Phi)$ in Equation (4). Since, the imaging signals may be wave encoded k-space data including the effect of the wave encoding gradient, the point spread function P may be added to Equation (4) to make the estimated imaging data relate to the wave encoding gradient (e.g., add the effect of the wave encoding gradient to the estimated imaging data), so as to offset the effect of the wave encoding gradient in the imaging signals d. For example, as illustrated above, the effect of the wave encoding gradient may be described as: each readout line in the underlying image is convolved with the PSF to yield the acquired wave image, or a multiplication of the sampled k-space and the PSF along the X direction to yield the wave encoded k-space data. Therefore, in Equation (4), "PF$_x$" may be added to make the estimated imaging data including the effect of the wave encoding gradient, thereby offset the effect of the wave encoding gradient in the imaging signals d.

In some embodiments, the coil sensitive map may indicate a plurality of coil sensitivities of a plurality of receiving coils of the MRI device 110.

In some embodiments, the processing device 120 (e.g., the obtaining module 510) may obtain a coil sensitivity of each of the plurality of receiving coils. In some embodiments, a receiving coil may correspond to a coil sensitivity. As used herein, the coil sensitivity of a receiving coil refers to a response degree of the receiving coil for receiving an input signal (e.g., an MR signal). In some embodiments, the coil sensitivity of a receiving coil may represent a spatial brightness change and/or a phase change introduced when an image is obtained by the receiving coil. In some embodiments, the coil sensitivity may be a complex number, and the modulus of the complex number may be between 0 and 1. In some embodiments, the coil sensitivity of the each receiving coil of the plurality of receiving coils in the MRI device may be the same or different.

In some embodiments, the coil sensitivity of the receiving coil may be determined based on a coil sensitivity algorithm. Exemplary coil sensitivity algorithms may include a sum of squares (SOS) algorithm, an estimating signal parameters via rotational invariance technique (ESPIRiT)-based algorithm, or the like.

In some embodiments, the processing device 120 may obtain the coil sensitivity map from one or more components (e.g., the MRI device 110, the terminal 140, and/or the storage device 130) of the MRI system 100 or an external storage device via the network 150. For example, the plurality of coil sensitivities of the plurality of receiving coils may be stored in the storage device 130, or any other storage device for storage. The processing device 120 may obtain the plurality of coil sensitivities of the plurality of receiving coils from the storage device 130, or any other storage device.

In 660, the processing device 120 (e.g., the reconstruction module 530) may generate one or more target images of the ROI based on the temporal information and the spatial information.

A target image of the ROI may be a static image and/or a dynamic image of the ROI. In some embodiments, the static image may correspond to a specific motion phase of the ROI. For example, the static image may include a 2D or 3D image of the ROI corresponding to a certain cardiac phase or a certain respiratory phase. The dynamic image may reflect dynamic information of the ROI along at least one time-varying dimension. In some embodiments, the dynamic image may include a series of 2D or 3D images over time, such as a plurality of 2D or 3D images of the ROI corresponding to a plurality of motion phases of the subject. For example, a dynamic image may reflect the cardiac motion of a cardiac slice or volume over a cardiac cycle, and include a plurality of images of the cardiac slice or volume corresponding to a plurality of cardiac phases in the cardiac cycle.

In some embodiments, the processing device 120 may generate a plurality of 3D static images of the ROI corresponding to at least one temporal dimension, and further generate a 4D dynamic image of the ROI corresponding to the at least one temporal dimension by combining the plurality of 3D static images of the ROI.

In some embodiments, the processing device 120 may generate a plurality of 2D static images of each slice of the ROI using, e.g., SMS imaging. The plurality of 2D static images may correspond to at least one temporal dimension. The processing device 120 may further generate a 3D dynamic image of the ROI corresponding to the at least one temporal dimension by combining the plurality of 2D static images of the slices of the ROI.

In some embodiments, the processing device 120 may generate a dynamic image corresponding to at least one temporal dimension for each slice of the ROI, and further generate a 3D dynamic image of the ROI by combining the dynamic images of the slices of the ROI.

As aforementioned, a target image of the ROI with multiple dimensions may be represented by a multi-dimensional tensor, which may be determined based on the spatial information (e.g., a spatial factor matrix including one or more spatial basis functions) of the ROI, the temporal information (e.g., one or more temporal factor matrices including one or more temporal basis functions) of the ROI, and the core tensor. For example, with the core tensor, the spatial information, and the temporal information available, the processing device 120 may generate the target image of the ROI with multiple time-varying dimensions by determining a product of the one or more temporal factor matrices of the one or more time-varying dimensions including the one or more temporal basis functions, the spatial factor matrix including the one or more spatial basis functions, and the core tensor that governs the interaction between the temporal factor matrices and the spatial factor matrix, e.g., determining a product of the spatial information, the temporal information, and the core tensor, i.e., the processing device 120 may generate the target image by performing multiplication of the spatial information, the temporal information, and the core tensor.

In some embodiments, the processing device 120 may generate a target image of the ROI corresponding to a certain time-varying dimension based on the temporal factor matrix corresponding to the certain time-varying dimension and the spatial factor matrix including the at least one spatial basis function. For example, the processing device 120 may generate a dynamic image of the ROI by determining a product of a spatial factor matrix including the spatial basis function(s) of the ROI, the temporal factor matrix including the temporal basis function(s) relating to the cardiac motion, and a core tensor that governs the interaction between the spatial factor matrix and the temporal factor matrix. As another example, the processing device 120 may further extract a static image of the ROI corresponding to a certain cardiac phase from the dynamic image of the ROI.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the process 1000 may be accomplished with one or more additional operations not described and/or without one or more of the operations discussed above. In some embodiments, the Equations provided above are illustrative examples and can be modified in various ways. For example, one or more coefficients in an Equation may be omitted, and/or the Equation may further include one or more additional coefficients.

Figure 7:
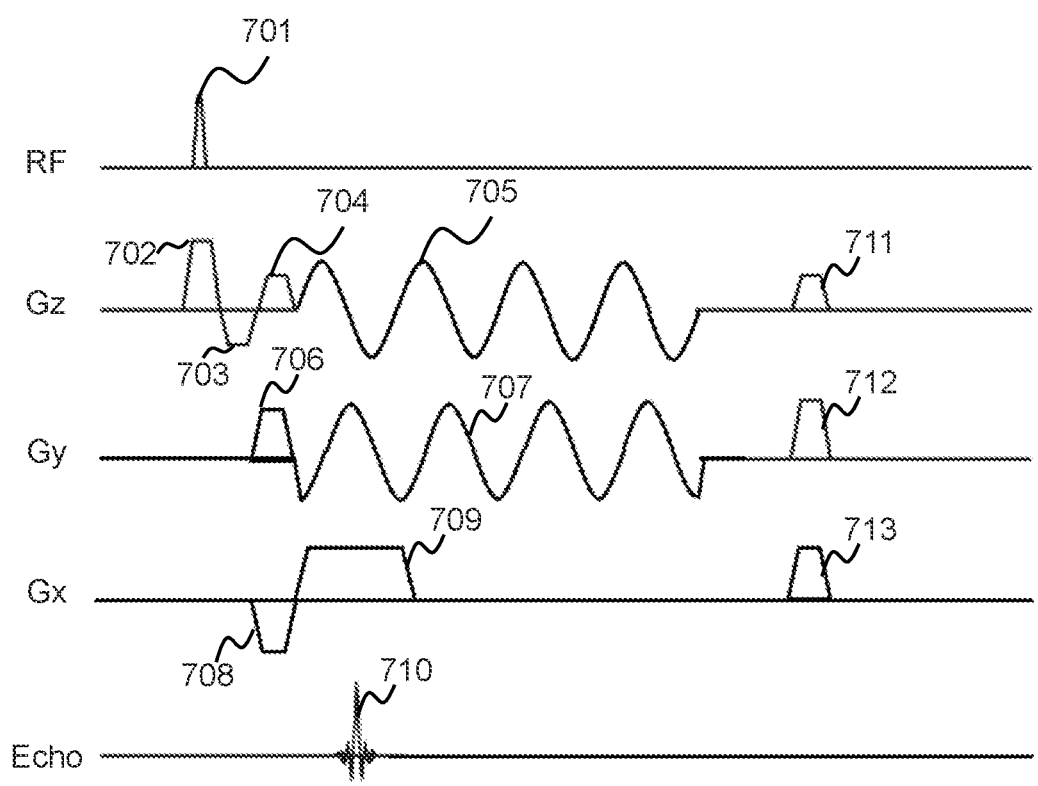
FIG. 7 is a schematic diagram of a pulse sequence for a single repetition time (TR) according to some embodiments of the present disclosure.

FIG. 7 is a schematic diagram of a pulse sequence 700 for a single repetition time (TR) according to some embodiments of the present disclosure. The repetition time (TR) may be between two consecutive excitation RF pulses. In some embodiments, the imaging signals may be acquired by applying, for one or more times, the 3D pulse sequence 700 to the ROI. In this case, the ROI may be a slab or a volume for 3D MRI imaging.

As shown in FIG. 7, the pulse sequence 700 may include an RF excitation pulse 701 that is played out in the presence of a slab-selective gradient 702 in order to produce transverse magnetization in the ROI. The slab-selective gradient 702 may be applied in a first direction. The slab-selective gradient 702 may include a rephasing lobe 703 that acts to rephase unwanted phase dispersions introduced by the slab-selective gradient 702 such that signal losses resultant from these phase dispersions are mitigated. Following excitation of the nuclear spins in the ROI, a phase encoding gradient 706 may be applied in a second direction to spatially encode a nuclear magnetic resonance echo signal 710. At the same time, a partition-encoding gradient 704 may be applied to spatially encode the echo signal 710 along the first direction. A readout gradient 709 may be applied after a dephasing gradient lobe 708 to spatially encode the echo signal 710 along a third direction. By way of example, the first direction may be a slice selection direction along the Y direction, the second direction may be a phase encoding direction along the Z direction, and the third direction may be a readout direction along the X direction. The echo signal 710 may be filled into the k-space during a data acquisition window.

Merely for illustration, only one echo is shown in FIG. 7. However, it should be noted that the pulse sequence 700 may also lead to a plurality of echoes in one TR.

In some embodiments, the pulse sequence 700 may further include a wave encoding gradient including a first oscillating encoding gradient 705 in the first direction and a second oscillating encoding gradient 707 in the second direction. During the application of the readout gradient 709, the first oscillating encoding gradient 705 may be applied along the first direction (e.g., the slice selection direction). At the same time, the second oscillating encoding gradient 707 may be applied along the second direction (e.g., the phase encoding direction). The first oscillating encoding gradient 705 and the second oscillating encoding gradient 707 may be applied during the acquisition of the echo 710. The combined effect of the first oscillating encoding gradient 705 and the second oscillating encoding gradient 707 being applied in the presence of the readout gradient 709 is to fill the echo 710 into the k-space along a corkscrew trajectory.

In some embodiments, spoiler gradients 711, 712, and 713 may be applied along the slice selective, phase-encoding, and frequency encoding directions, respectively, to dephase any residual transverse magnetization in the ROI to prevent signal contamination from one repetition time period to the next.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 8:
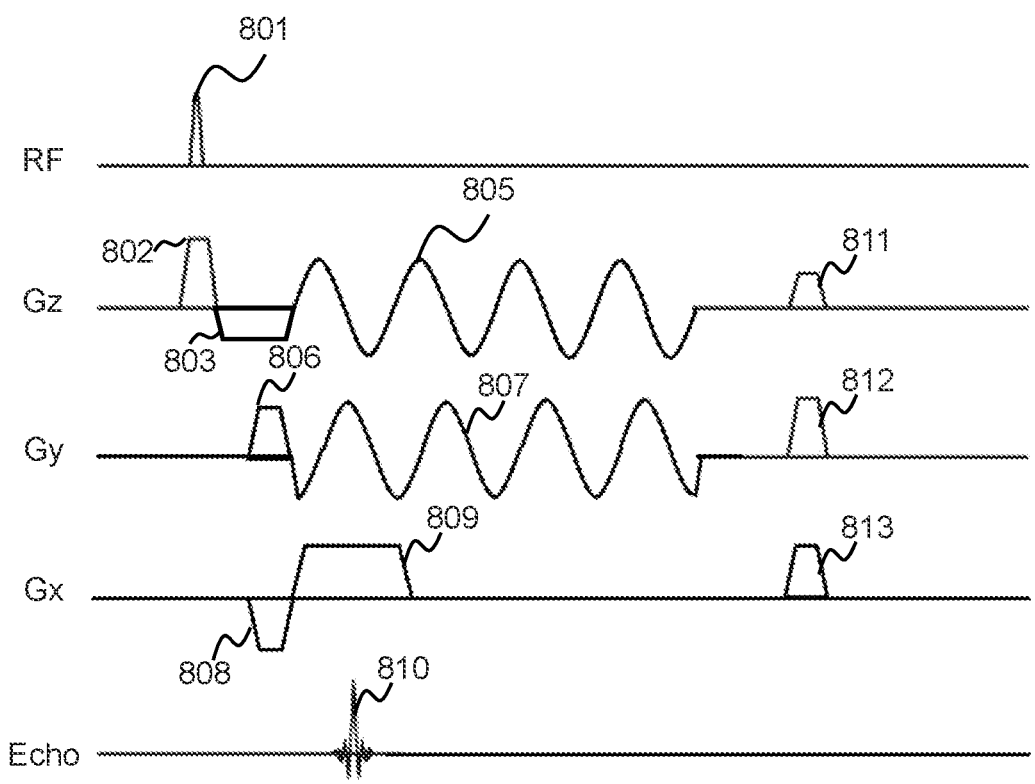
FIG. 8 is a schematic diagram of a pulse sequence for a TR according to some embodiments of the present disclosure.

FIG. 8 is a schematic diagram of a pulse sequence 800 for a single repetition time (TR) according to some embodiments of the present disclosure. In some embodiments, the imaging signals may be acquired by 2D acquisition with simultaneously excitation of multiple slice locations (e.g., simultaneous multi-slice (SMS) technique) of the ROI by applying, for one or more times, the pulse sequence 800 to the ROI. In this case, the ROI may include a plurality of slices for 2D SMS imaging.

The pulse sequence 800 may include a spatially-selective RF excitation pulse 801 (e.g., a multiband RF pulse) that is played out in the presence of a slice-selective gradient 802 in order to produce transverse magnetization in a plurality of prescribed imaging slices of the ROI. The slice-selective gradient 802 may include a rephasing lobe 803 that acts to rephase unwanted phase dispersions introduced by the slices elective gradient 802 such that signal losses resultant from these phase dispersions are mitigated. Following excitation of the nuclear spins in the prescribed imaging slices of the ROI, a phase encoding gradient 806 may be applied to spatially encode a nuclear magnetic resonance signal representative of an echo 810 along the second direction (e.g., the phase encoding direction) in the prescribed imaging slices. A readout gradient 809 may be applied after a dephasing gradient lobe 808 to spatially encode the echo 810 along the third direction (e.g., the readout direction) in the prescribed imaging slices. The echo 810 may be filled into the k-space during a data acquisition window.

Merely for illustration, only one echo is shown in FIG. 8. However, it should be noted that the pulse sequence 800 may also lead to a plurality of echoes in one TR.

In some embodiments, the pulse sequence 800 may further include a wave encoding gradient including a first oscillating encoding gradient 805 in the first direction (e.g., the slice selection direction) and a second oscillating encoding gradient 807 in the second direction. During the application of the readout gradient 809, the first oscillating encoding gradient 805 may be applied along the first direction (e.g., the slice selection direction). At the same time, the second oscillating encoding gradient 807 may be applied along the second direction (e.g., the phase encoding direction). The first oscillating encoding gradient 805 and the second oscillating encoding gradient 807 may be applied during the acquisition of the echo 810.

Seen from the imaging plane of each slice location and across the multiple simultaneously excited slice locations of the ROI, the combined effect of the first oscillating encoding gradient 805 and the second oscillating encoding gradient 807 being applied in the presence of the readout gradient 809 is to produce a corkscrew sampling trajectory.

In some embodiments, spoiler gradients 811, 812, and 813 may be applied along the slice selective, phase-encoding, and frequency encoding directions, respectively, to dephase any residual transverse magnetization in the multiple slice locations of the ROI to prevent signal contamination from one TR period to the next.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
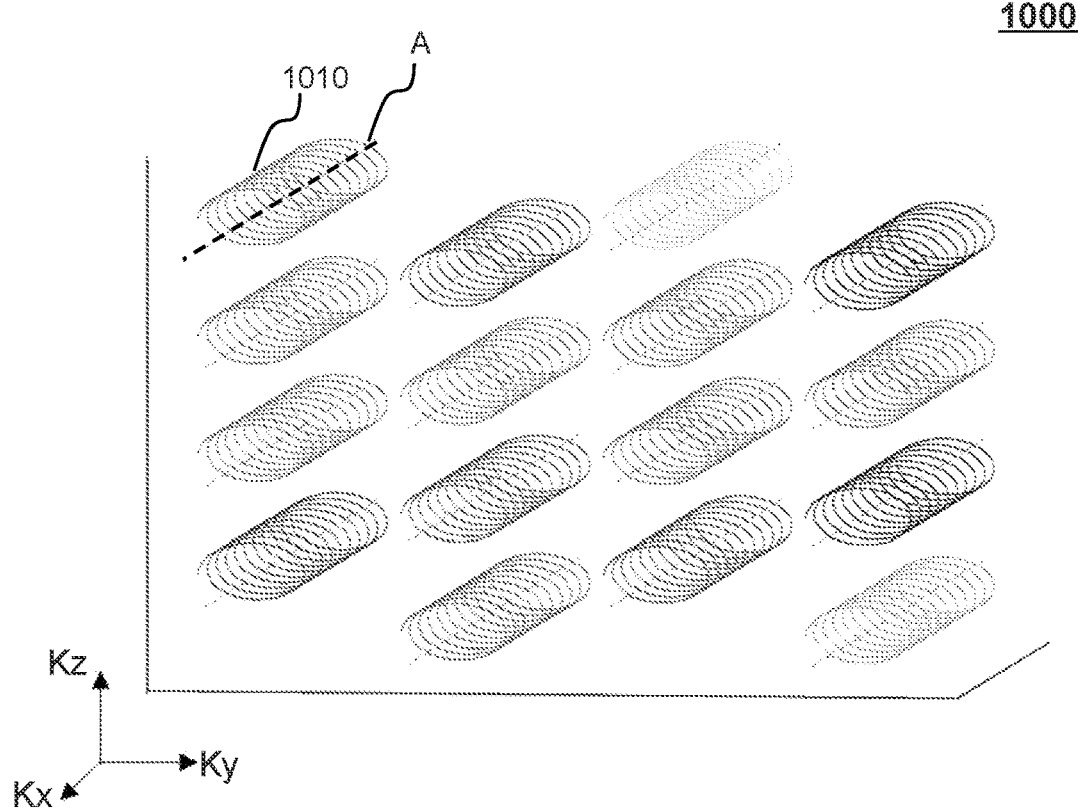
FIG. 10 is a schematic diagram illustrating an exemplary corkscrew sampling pattern according to some embodiments of the present disclosure.

FIG. 9 is a schematic diagram illustrating an exemplary Cartesian sampling pattern 900 according to some embodiments of the present disclosure. FIG. 10 is a schematic diagram illustrating an exemplary corkscrew sampling pattern 1000 according to some embodiments of the present disclosure.

As illustrated in FIGS. 9 and 10, Kx represents a readout direction, Ky represents a phase encoding direction, and Kz represents a slice selection direction.

As illustrated in FIG. 9, the first pulse sequence excluding the wave encoding gradient (e.g., the pulse sequence 700 excluding the first oscillating encoding gradient 705 and the second oscillating encoding gradient 707) may lead to a first sampling trajectory that is a Cartesian sampling trajectory. The Cartesian sampling trajectory may include a plurality of straight trajectories along the Kx direction.

As illustrated FIG. 10, the first pulse sequence including the wave encoding gradient (e.g., the pulse sequence 800 excluding the first oscillating encoding gradient 805 and the second oscillating encoding gradient 807) may lead to a second sampling trajectory that is the corkscrew sampling pattern including a plurality of corkscrew trajectories along the Kx direction. A central axis of each corkscrew trajectory (e.g., a central axis A of a corkscrew trajectory 1010) is parallel to the Kx direction. For example, each corkscrew trajectory may be around one of the straight trajectories in the Cartesian sampling pattern 900 in FIG. 9.

In some embodiments, the first pulse sequence excluding the wave encoding gradient may also lead to a non-Cartesian sampling pattern. Exemplary non-Cartesian sampling pattern may include a spiral sampling pattern, a radial sampling pattern, a zigzag sampling pattern, a propeller sampling pattern, or the like.

For example, if the first pulse sequence excluding the wave encoding gradient leads to a radial sampling pattern including a plurality of radial trajectories (e.g., radial straight lines or radial curved lines), the first pulse sequence including the wave encoding gradient may lead to a corkscrew sampling pattern including a plurality of corkscrew trajectories. Each of the plurality of corkscrew trajectories may be around one of the plurality of radial trajectories of the radial sampling pattern.

As another example, if the first pulse sequence excluding the wave encoding gradient leads to a spiral sampling pattern including one or more spiral trajectories, the first pulse sequence including the wave encoding gradient may lead to a corkscrew sampling pattern including one or more corkscrew trajectories. Each of the one or more trajectories may be around one of the one or more spiral trajectories of the spiral sampling pattern.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the imaging signals and the auxiliary signals may be acquired by 2D acquisition with simultaneously excitation of multiple slice locations (e.g., simultaneous multi-slice (SMS) technique) of the ROI. For each of the multiple slice locations, the processing device 120 may generate one or more target images of the slice location based on the auxiliary signals and the imaging signals.

In some embodiments, to implement the SMS technique, the MRI scanner may include at least one excitation pulse (e.g., multi-band RF pulse(s)) for exciting the slice locations simultaneously and a phase modulation scheme for facilitating slice separation from aliasing image data in image reconstruction.

In some embodiments, during the application of the MRI pulse sequence, phase modulation may be applied to at least one of the slice locations so that the plurality of slice locations have different phases during the readout of at least one of the plurality of imaging signals. As used herein, if at least two of the plurality of slice locations have different phases, the plurality of slice locations may be regarded as having different phases. In other words, during the readout of the at least one of the imaging signals, the phases of the slice locations may be partially or completely different from each other. In some embodiments, during the application of the MRI pulse sequence, phase modulation may be applied to each of the slice locations or a portion of the slice locations.

For example, the phase modulation may be applied to the at least one slice location so that the at least one slice location has a random phase during the readout of each of the plurality of imaging signals. As another example, the phase modulation may be applied to the at least one slice location so that the phase of the at least one slice location alternates between a first degree and a second degree during the readout of consecutive imaging signals of the plurality of imaging signals, wherein the second degree is different from the first degree. As still another example, the slice locations may include three slice locations, and phase modulation may be applied to two of the three slice locations, so that the phase of one slice (e.g., a first slice) location is always 0°, the phase of one slice (e.g., a second slice) location changes from −120° to 0° to 120° periodically, and the phase of one slice (e.g., a third slice) location changes from −240° to 0° to 240° periodically.

The processing device 120 may determine the temporal basis function(s) relating to the time-varying dimension(s) of the slice location based on the auxiliary signals. In some embodiments, the processing device 120 may determine the temporal basis function(s) of the time-varying dimension(s) based on the auxiliary signals obtained in operation 640.

In some embodiments, for different slice locations, the temporal basis functions relating to a time-varying dimension may be the same if the target slice locations have the same dynamic change or similar dynamic changes along the time-varying dimension. Merely by way of example, different cardiac slices may share the same cardiac temporal basis function(s) because they follow similar laws of motion in a cardiac cycle. In such cases, operation 640 may only need to be performed once to determine the cardiac temporal basis function(s) of the cardiac slices, and the cardiac temporal basis function(s) may be used to generate target images of different cardiac slices.

The processing device 120 may determine the spatial basis function(s) relating to the spatial-varying dimension(s) of the slice location based on the temporal basis function(s) and the imaging signals. In some embodiments, the principle of determining the spatial basis function(s) of multiple slice locations may be similar to the principle of determining the spatial basis function(s) in operation 650. In some embodiments, for different slice locations, the point spread function may be the same because the same wave encoding gradient is applied to the slice locations.

Merely by way of example, different cardiac slices may share the same cardiac temporal basis function(s) because they follow similar laws of motion in a cardiac cycle. In such cases, operation 640 may only need to be performed once to determine the cardiac temporal basis function(s) of the cardiac slices, and the cardiac temporal basis function(s) may be used to generate target images of different cardiac slices.

For example, the imaging signals and the auxiliary signals may be acquired by 2D acquisition with simultaneously excitation of slice locations 1 and 2. Phase modulation may be applied to the slice location 2 so that the slice location 2 has a random phase during the readout of each of the imaging signals. The processing device 120 may determine the spatial basis functions of slice locations 1 and 2 according to Equation (5) as below:

$$\widehat{U_1}, \widehat{U_2} = \mathrm{argmin}\|d_{img} - \Omega F P F_x(S_1 U_1 \Phi + S_2 U_2 \Phi P_r)\|_2^2 + R(U_1, U_2), \quad (5)$$

where $\widehat{U_1}$ represents an optimal spatial factor matrix of the slice location 1 determined by solving Equation (5), $\widehat{U_2}$ represents an optimal spatial factor matrix of the slice location 2 determined by solving Equation (5), $U_1$ represents estimated spatial factor matrix (e.g., the estimated spatial information) of the slice location 1, $U_2$ represent estimated spatial factor matrix (e.g., the estimated spatial information) of the slice location 2, $d_{img}$ represents the imaging signals of the slice locations 1 and 2, $\Omega$ represents an undersampling operator, F represents a Fourier transformation operator, $S_1$ represents a coil sensitive map corresponding to the slice location 1, $S_2$ represents a coil sensitive map corresponding to the slice location 2, $\Phi$ represents a product of the core tensor and the one or more temporal factor matrices, $P_r$ represents a random phase operator applied on the slice location 2, and $R(U_1, U_2)$ represents a constraint item relating to the spatial factor matrices of the slice locations 1 and 2 (which may be omitted in some conditions), P represents the point spread function (e.g., determined based on operation 630) corresponding to the wave encoding gradient applied to acquire the imaging signals, and $F_x$ represents a Fourier transformation along the X direction (e.g., the readout direction). In some embodiments, $P_r$ may include a plurality of operators $P_i$ each of which is applied to a readout line i. For example, $P_i = \exp(\sqrt{-1} * \theta_i)$, wherein $\theta_i$ represents a random phase applied on a readout line i of the slice location 2. In some embodiments, the comparison item of Equation (4) may include $\mathrm{argmin}\|d_{img} - \Omega F P F_x(S_1 U_1 \Phi + S_2 U_2 \Phi P_r)\|_2^2$. The determined $\widehat{U_1}$ and $\widehat{U_2}$ may include the determined spatial basis function(s) of the slice location 1 and the determined spatial basis function(s) of the slice location 2, respectively.

As another example, the imaging signals and the auxiliary signals may be acquired by 2D acquisition with simultaneously excitation of slice locations 1 and 2, and phase modulation may be applied to the slice location 2 so that the phase of the slice location 2 alternates between 0 degree and 180 degrees during the readout of consecutive imaging signals of the plurality of imaging signals. The processing device 120 may determine the spatial basis functions of the slice locations 1 and 2 according to Equations (6) and (7) as below, respectively:

$$\widehat{U_1} = \mathrm{argmin}\|(d_{img}^+ + d_{img}^-)/2 - \Omega F F P_x S_1 U_1 \Phi\|_2^2 + R(U_1), \quad (6)$$

$$\widehat{U_2} = \mathrm{argmin}\|(d_{img}^+ - d_{img}^-)/2 - \Omega F P F_x S_2 U_2 \Phi\|_2^2 + R(U_2), \quad (7)$$

where $d_{img}^+$ represents the imaging signals acquired when the phases of the slice locations 1 and 2 are both 0°, $d_{img}^-$ represents the imaging signals acquired when the phases of the slice locations 1 and 2 are 0° and 180°, respectively. In some embodiments, the comparison item of Equation (6) may include $\mathrm{argmin}\|(d_{img}^+ + d_{img}^-)/2 - \Omega FPF_x S_1 U_1 \Phi\|_2^2$, and the comparison item of Equation (7) may include $\mathrm{argmin}\|(d_{img}^+ - d_{img}^-)/2 - \Omega FPF_x S_2 \Phi_2\|_2^2$.

The processing device 120 may generate one or more target images of the slice location based on the temporal basis function(s) and the spatial basis function(s) of the target slice location.

In some embodiments, the target images of multiple slice locations may be generated simultaneously by performing a process similar to the above process.

The present disclosure provides an imaging technique that combines the advantages of the SMS technique, the multitasking technique, and the wave encoding technique. By further introducing the SMS imaging technique, the scanning time can be shortened, and/or the accuracy of the dynamic tracking with respect to some portions that don't have obvious motion (e.g., slice locations near the apex where cardiac contractions and relaxations are not obvious) can be improved.

It should be noted that the above description regarding the process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 11A:
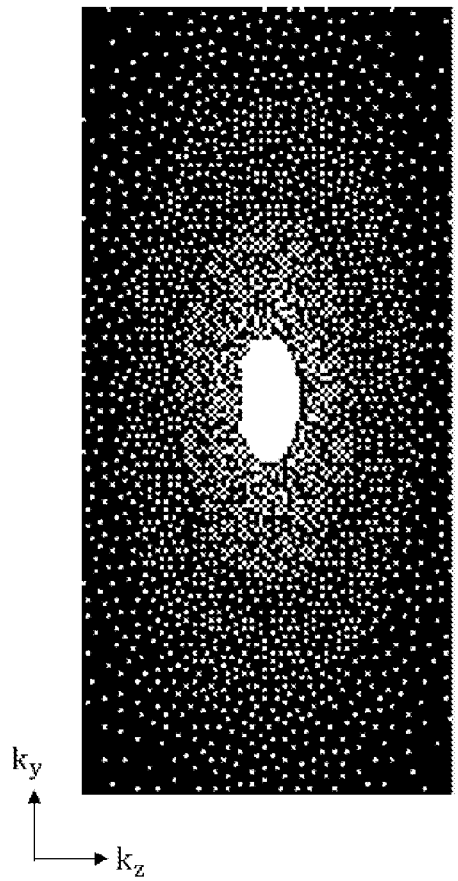
FIG. 11A is a schematic diagram illustrating an exemplary variable density sampling pattern according to some embodiments of the present disclosure.

The variable density undersampling may have a potential in reducing aliasing artifacts and improving sampling efficiency. In some embodiments, the variable density undersampling may allow the sampling density to be a function of the k-space location, as illustrated in FIG. 11A. This may enable a flexible allocation of the scan time based on signal characteristics, scan time constraints, and/or the image quality suitable for a specific application. Data in the central k-space region may correspond to structural features associated with a subject to be scanned, and data in the outer k-space region may correspond to detailed features associated with the subject. In some embodiments, the variable density undersampling may sufficiently sample the central k-space region to reduce low-frequency aliasing artifacts, and undersample the outer k-space region to reduce the scan time while maintaining or increasing the image quality in terms of, e.g., the spatial resolution. For example, the sampling density in the central k-space region may be relatively high, and the sampling density in the outer k-space region may be relatively low. As used herein, a sampling density refers to a number (or count) of sampled data points per unit area of the k-space. The acceleration factor of the variable density undersampling for different portions of the k-space may be any value, for example, 2, 3, 4, 5, 6, 10, or the like. In some embodiments, the acceleration factor of an undersampling pattern, e.g., a variable density undersampling pattern, a uniform undersampling pattern, may be a ratio of the amount of k-space data needed for a fully sampled k-space to the amount of k-space data sampled according to the undersampling pattern.

In some embodiments, the target set of k-space data may be obtained by filling the target MR signals into the k-space along a variable density corkscrew trajectory or a random corkscrew trajectory. As used herein, a variable density corkscrew trajectory refers to that a plurality of corkscrew trajectories corresponding to a target set of k-space data are distributed in the k-space with variable densities. As used herein, a random corkscrew trajectory refers to that a plurality of corkscrew trajectories corresponding to a target set of k-space data are randomly distributed in the k-space.

Since the acceleration factor of the variable density undersampling can be any suitable value, the setting of the acceleration factor in the variable-density wave acquisition and reconstruction algorithm may be relatively flexible. In addition, when the acceleration factor is the same (especially when the acceleration factor is relatively high, e.g., higher than 6) as a uniform undersampling pattern (e.g., the CAIPIRINHA sampling pattern), the quality of the target image (e.g., a signal-to-noise ratio of the target image) generated based on k-space data obtained using the variable-density undersampling pattern may be relatively high compared to the uniform undersampling pattern. Since the uniform undersampling does not consider the conjugate symmetry of the K-space data, and the variable density undersampling can sufficiently sample the central k-space region (i.e., a low frequency region) and undersample a conjugate symmetry region, the efficiency of the variable density sampling may be relatively high, and the quality of the target image generated based on k-space data obtained using the variable-density undersampling pattern may be relatively high compared to the uniform undersampling pattern.

Furthermore, a random wave acquisition and reconstruction method may also be provided in the present disclosure. As used herein, a random wave acquisition and reconstruction refers to that k-space data used for MRI image reconstruction is obtained by filling MR signals into the k-space along a random corkscrew trajectory. A compressed sensing technique may be used in the reconstruction of a target image for correcting random artifacts generated in the random undersampling (i.e., the random corkscrew trajectory), which may further improve the quality of the target image.

In some embodiments, if the corkscrew sampling pattern is a uniform corkscrew trajectory, the plurality of corkscrew trajectories may be uniformly distributed in the k-space. For example, a distance between central axes of adjacent corkscrew trajectories may be the same. In some embodiments, if the corkscrew sampling pattern is a random corkscrew trajectory, the plurality of corkscrew trajectories may be randomly distributed in the k-space. For example, a distance between central axes of adjacent corkscrew trajectories may be different.

In some embodiments, if the corkscrew sampling pattern is a variable density corkscrew trajectory, the plurality of corkscrew trajectories may be distributed in the k-space with variable densities. For example, in the Ky direction and/or the Kz direction, a sampling density may change over the k-space location. The sampling density in a central k-space region may be relatively high, and the sampling density in an outer k-space region may be relatively low, as illustrated in FIG. 11A.

Figure 11B:
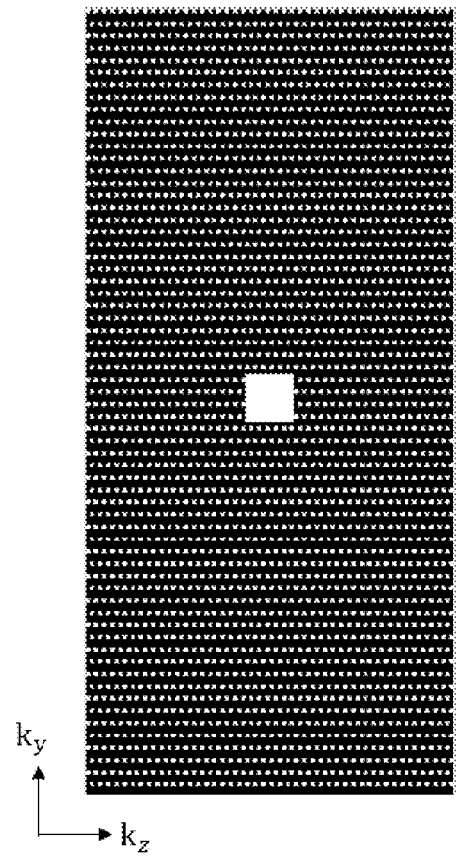
FIG. 11B is a schematic diagram illustrating an exemplary uniform sampling pattern according to some embodiments of the present disclosure.

FIG. 11A is a schematic diagram illustrating an exemplary variable density sampling pattern according to some embodiments of the present disclosure. FIG. 11B is a schematic diagram illustrating an exemplary uniform sampling pattern according to some embodiments of the present disclosure.

As illustrated in FIGS. 11A and 11B, Ky represents a phase encoding direction, Kz represents a slice selection direction, and a white dot refers to a sampled data point in k-space. As illustrated in FIG. 11A, for the variable density sampling pattern, in both the Ky direction and the Kz direction, a sampling density changes over the k-space location. As illustrated, the sampling density in a central k-space region may be relatively high, and the sampling density in an outer k-space region may be relatively low. For example, the central k-space region may be fully sampled, and the outer k-space region may be undersampled. In a Kx direction (not shown in FIG. 11A), the k-space may be fully sampled or undersampled. As illustrated in FIG. 11B, for the CAIPIRINHA sampling pattern, in both the Ky direction and the Kz direction, the k-space is undersampled. In the Kx direction (not shown in FIG. 11B), the k-space may be fully sampled or undersampled.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, for the process 600, in operation 620, the processing device 120 may extract a portion of the plurality of imaging signals as the auxiliary signals. In this way, no additional acquisition is required to acquire the auxiliary signals. In operation 640, the processing device 120 may determine, based on the portion of the plurality of imaging signals, temporal information relating to at least one temporal dimension of the ROI.

In some embodiments, the processing device 120 may determine a plurality of reference images based on a portion of the plurality of imaging signals of which frequencies meet specific requirements, or of which spatial positions in the k-space meet specific requirements, or that are determined based on other algorithm rules.

In some embodiments, the reference images may be reconstructed based on a portion of the plurality of imaging signals of which the frequencies are lower than a frequency threshold. The frequency threshold may be determined according to actual needs or experience, for example, 120 Hz or 130 Hz, as another example, 0.08 Hz or 0.09 Hz. In some embodiments, the frequency threshold may be determined according to the magnetic resonance frequency range corresponding to the scanned object. For example, the threshold corresponding to the low frequency part of the frequency range may be determined as the frequency threshold.

In some embodiments, the reference images may be reconstructed based on a portion of the plurality of imaging signals located in the central area of the k-space. The central area may be be determined according to actual needs or experience. For example, taking the center point of k-space as the origin, and the spatial region where the value corresponding to the frequency in the space coordinate is from 0 to 120 Hz is the central region. It can be understood that the frequency corresponding to the central area of the k-space is lower than the frequency threshold.

In some embodiments, the portion of the plurality of imaging signals may be acquired corresponding to multiple times. A reference image may be reconstructed based on the portion of the plurality of imaging signals corresponding to one time.

In some embodiments, the imaging signals may be acquired based on a plurality of spiral trajectories with a reduced density from the center to the outside in the k-space, that is, the k-space data track density in the center of the k-space is greater than the k-space data track density in the surrounding part of the k-space.

In some embodiments, among the plurality of spiral trajectories, at least two spiral trajectories corresponding to adjacent times have a rotation angle.

In some embodiments, the processing device 120 may determine an image representation matrix based on the multiple reference images and the multiple time sequences corresponding to the multiple reference images. The image representation matrix may include a space dimension and a time dimension. The space dimension may correspond to the spatial position in the reference images, and the time dimension may represent the multiple times corresponding to the multiple reference images.

In some embodiments, a reference image may be expressed as a vector, and based on the time sequence of multiple times corresponding to multiple reference images, multiple vectors corresponding to multiple reference images may be sequentially arranged to obtain the corresponding image representation matrix.

In some embodiments, a reference image may be represented as a row vector, and multiple row vectors corresponding to the multiple reference images may be arranged in a sequence based on a time sequence along the column direction to obtain an image representation matrix. In some embodiments, a reference image may be represented as a column vector, and multiple column vectors corresponding to the multiple reference images may be sequentially arranged along the row direction based on a time sequence to obtain an image representation matrix.

For a reference image, it may include m*n pixels, and m and n are integers. Each pixel includes pixel information (for example, the spatial location of the pixel, pixel value, etc.). In some embodiments, the reference image including m*n pixels may be represented as a vector including m*n elements, and each element in the vector may correspond to the pixel information of one pixel (such as the spatial position of the pixel). In the image representation matrix, the spatial position information (such as the spatial position of a pixel) and time information (such as the scanning time corresponding to the multiple reference images) of multiple reference images may be included.

It can be understood that based on the arrangement of the vector representation and the image representation matrix corresponding to the reference image, the row dimension and column dimension of the image matrix correspond to the space dimension and time dimension of the multiple reference images, respectively. The spatial dimension corresponds to the spatial position information in the reference image, and the time dimension represents the time information of multiple reference images, that is, multiple times corresponding to the multiple reference images.

In some embodiments, the processing device 120 may determine the time information based on the image representation matrix and the time dimension.

As mentioned above, the image representation matrix may include spatial information (such as the spatial position of a pixel) and time information (such as multiple times corresponding to the multiple reference images) of multiple reference images. The row dimension and column dimension of the image matrix correspond to the space dimension and time dimension of multiple reference images, respectively.

In some embodiments, the image representation matrix can be matrix decomposed to obtain the first matrix corresponding to the time dimension (that is, the matrix representing the time information of the reference images) and the second matrix corresponding to the space dimension (that is, the reference images matrix of spatial information). In some embodiments, the first matrix obtained by decomposition (that is, the matrix representing the time information of the reference images) may include the time information of multiple reference images (such as multiple times corresponding to the multiple reference images), and the second matrix (that is, representing the matrix of reference image spatial information) may include spatial information of multiple reference images (such as the spatial positions of pixels in the reference images).

In some embodiments, the time information of the dynamic image may be determined based on the first matrix. In some embodiments, the time information basis of the dynamic image may be determined based on the first matrix, and the time information basis of the dynamic image can be used as the time information of the dynamic image.

In some embodiments, the rank of the first matrix may be determined, and a part of the first matrix may be determined based on the rank of the first matrix as a representation of the temporal basis of the dynamic image. In some embodiments, the rank of the matrix may be obtained by solving the matrix. For example, the elementary transformation method, Gaussian elimination method and other algorithms are used to obtain the rank of the matrix. In some embodiments, the rank of the matrix corresponds to a value range, which can be set according to experience or actual needs. For example, the value range may be 10-40. Take the rank of 20 as an example, that is, the first 20 columns of the second matrix are used as the representation of the time basis of the dynamic image. It can be understood that the rank of the matrix is smaller than the column dimension of the matrix. In some embodiments, the rank of the matrix is related to the temporal correlation or similarity between multiple reference images.

In some embodiments, the matrix decomposition of the image representation matrix may adopt a manner of performing singular value decomposition on the image representation matrix based on the time dimension to determine the time information of the dynamic image. For example, by performing singular value decomposition, the image representation matrix may be represented based on an orthogonal matrix corresponding to the row dimension, an orthogonal matrix corresponding to the column dimension, and a diagonal matrix. The orthogonal matrix corresponding to the time dimension obtained by decomposition may be used as the first matrix corresponding to the time dimension (that is, the matrix representing time information).

More Details regarding determining the temporal information based on a portion of the plurality of imaging signals without additional acquisition of auxiliary signals may be found in, for example, Chinese application No. 202110478711.X, which is incorporated herein by reference.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages.

The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method for magnetic resonance imaging (MRI) implemented on a computing device having at least one processing device and at least one storage device, the method comprising:
    obtaining a plurality of imaging signals collected by applying a wave encoding gradient to a region of interest (ROI) of a subject;
    obtaining a plurality of auxiliary signals associated with the ROI;
    obtaining a point spread function corresponding to the wave encoding gradient;
    determining, based on the plurality of auxiliary signals, temporal information relating to at least one temporal dimension of the ROI, the temporal information including at least one temporal basis function relating to the at least one temporal dimension;
    determining, based on the temporal information, the plurality of imaging signals, and the point spread function, spatial information relating to at least one spatial dimension of the ROI, the spatial information including at least one spatial basis function relating to the at least one spatial dimension; and
    generating at least one target image of the ROI based on the temporal information and the spatial information.

2. The method of claim 1, wherein the wave encoding gradient leads to a corkscrew trajectory in the k-space, the wave encoding gradient includes a first oscillating encoding gradient in a first direction and a second oscillating encoding gradient in a second direction, and a phase difference between the first oscillating encoding gradient and the second oscillating encoding gradient is configured to affect a rotation angle of the corkscrew trajectory.

3. The method of claim 1, wherein the plurality of imaging signals are obtained by filling target magnetic resonance (MR) signals into the k-space with variable densities or a uniform density.

4. The method of claim 1, wherein obtaining the point spread function corresponding to the wave encoding gradient includes:
generating a first image based on a first set of k-space data, wherein the first set of k-space data is obtained without applying the wave encoding gradient to the ROI;
generating a second image based on a second set of k-space data, wherein the second set of k-space data is obtained by applying the wave encoding gradient to the ROI, the first set of k-space data and the second set of k-space data corresponding to the same region in the k-space; and
determining the point spread function based on the first image and the second image.

5. The method of claim 1, wherein determining, based on the temporal information, the plurality of imaging signals, and the point spread function, the spatial information relating to the spatial dimension of the ROI includes:
constructing a target function based on the plurality of imaging signals, the temporal information, and the point spread function; and
determining the spatial information by solving the target function.

6. The method of claim 5, wherein determining the spatial information by solving the target function includes:
determining estimated spatial information;
determining estimated imaging data based on the estimated spatial information, the point spread function, and the temporal information, the point spread function being configured to make the estimated imaging data involve an effect of the wave encoding gradient;
determining a difference between the plurality of imaging signals and the estimated imaging data; and
determining the spatial information by solving, based on the difference, the target function.

7. The method of claim 6, wherein the target function includes
a comparison item configured to limit the difference between the plurality of imaging signals and the estimated imaging data, the comparison item including the point spread function; and
a regularization item configured to limit the estimated spatial information, the regularization item being a total variation of the spatial dimension of the estimated spatial information.

8. The method of claim 1, wherein the plurality of auxiliary signals and the plurality of imaging signals are acquired interleaved during an MRI scan of the subject, including:
acquiring the plurality auxiliary signals by repeatedly sampling a same location of a k-space; and
performing every sampling of the same location of the k-space before, after, or during a sampling of a first count of corkscrew trajectories.

9. The method of claim 1, wherein the target image is expressed by a product of a core tensor and (N+1) basis matrices according to a low-rank tensor image model, wherein
the core tensor is configured to govern an interaction between the (N+1) basis matrices,
the (N+1) basis matrices include a spatial factor matrix and N temporal factor matrix or matrices,
the spatial factor matrix includes one or more spatial basis functions relating to the at least one spatial dimension of the ROI, and
each of the N temporal factor matrix or matrices corresponds to one of the at least one temporal dimension and includes one or more temporal basis functions relating to a corresponding temporal dimension.

10. The method of claim 4, wherein the point spread function is determined based on a division between the first image and the second image.

11. The method of claim 4, wherein the determining the point spread function based on the first image and the second image, including:
determining a first phase matrix of the first image based on values of pixels or voxels in the first image, wherein a value in the first phase matrix of the first image is a phase value of a corresponding pixel or voxel in the first image;
determining a second phase matrix of the second image based on values of pixels or voxels in the second image, wherein a value in the second phase matrix of the second image is a phase value of a corresponding pixel or voxel in the second image; and
determining a phase difference matrix between the first phase matrix of the first image and the second phase matrix of the second image as the point spread function by determining a ratio between the first phase matrix of the first image and the second phase matrix of the second image.

12. A system for magnetic resonance imaging (MRI), comprising:
at least one storage device including a set of instructions; and
at least one processor in communication with the at least one storage device, wherein when executing the set of instructions, the at least one processor is directed to cause the system to perform operations including:
obtaining a plurality of imaging signals collected by applying a wave encoding gradient to a region of interest (ROI) of a subject;
obtaining a plurality of auxiliary signals associated with the ROI;
obtaining a point spread function corresponding to the wave encoding gradient;
determining, based on the plurality of auxiliary signals, temporal information relating to at least one temporal dimension of the ROI, the temporal information including at least one temporal basis function relating to the at least one temporal dimension;
determining, based on the temporal information, the plurality of imaging signals, and the point spread function, spatial information relating to at least one spatial dimension of the ROI, the spatial information including at least one spatial basis function relating to the at least one spatial dimension; and
generating at least one target image of the ROI based on the temporal information and the spatial information.

13. The system of claim 12, wherein the wave encoding gradient leads to a corkscrew trajectory in the k-space, the wave encoding gradient includes a first oscillating encoding gradient in a first direction and a second oscillating encoding gradient in a second direction, and a phase difference between the first oscillating encoding gradient and the second oscillating encoding gradient is configured to affect a rotation angle of the corkscrew trajectory.

14. The system of claim 12, wherein the plurality of imaging signals are obtained by filling target magnetic resonance (MR) signals into the k-space with variable densities.

15. The system of claim 12, wherein the plurality of imaging signals are obtained by filling target magnetic resonance (MR) signals into the k-space with a uniform density.

16. The system of claim 12, wherein obtaining the point spread function corresponding to the wave encoding gradient includes:
  generating a first image based on a first set of k-space data, wherein the first set of k-space data is obtained without applying the wave encoding gradient to the ROI;
  generating a second image based on a second set of k-space data, wherein the second set of k-space data is obtained by applying the wave encoding gradient to the ROI, the first set of k-space data and the second set of k-space data corresponding to the same region in the k-space; and
  determining the point spread function based on the first image and the second image.

17. The system of claim 12, wherein determining, based on the temporal information, the plurality of imaging signals, and the point spread function, the spatial information relating to the spatial dimension of the ROI includes:
  constructing a target function based on the plurality of imaging signals, the temporal information, and the point spread function; and
  determining the spatial information by solving the target function.

18. The system of claim 17, wherein determining the spatial information by solving the target function includes:
  determining estimated spatial information;
  determining estimated imaging data based on the estimated spatial information, the point spread function, and the temporal information, the point spread function being configured to make the estimated imaging data involve an effect of the wave encoding gradient;
  determining a difference between the plurality of imaging signals and the estimated imaging data; and
  determining the spatial information by solving, based on the difference, the target function.

19. The system of claim 18, wherein the target function includes
  a comparison item configured to limit the difference between the plurality of imaging signals and the estimated imaging data, the comparison item including the point spread function; and
  a regularization item configured to limit the estimated spatial information, the regularization item being a total variation of the spatial dimension of the estimated spatial information.

20. A non-transitory computer readable medium, comprising at least one set of instructions, wherein when executed by one or more processors of a computing device, the at least one set of instructions causes the computing device to perform a method, the method comprising:
  obtaining a plurality of imaging signals collected by applying a wave encoding gradient to a region of interest (ROI) of a subject;
  obtaining a plurality of auxiliary signals associated with the ROI;
  obtaining a point spread function corresponding to the wave encoding gradient;
  determining, based on the plurality of auxiliary signals, temporal information relating to at least one temporal dimension of the ROI, the temporal information including at least one temporal basis function relating to the at least one temporal dimension;
  determining, based on the temporal information, the plurality of imaging signals, and the point spread function, spatial information relating to at least one spatial dimension of the ROI, the spatial information including at least one spatial basis function relating to the at least one spatial dimension; and
  generating at least one target image of the ROI based on the temporal information and the spatial information.

* * * * *